US012767684B2

(12) United States Patent
Baevsky et al.

(10) Patent No.: US 12,767,684 B2
(45) Date of Patent: Oct. 20, 2026

(54) COMPOUNDS AND COMPOSITIONS FOR DIFFERENTIAL MODULATION OF NICOTINAMIDE ADENINE DINUCLEOTIDE

(71) Applicant: Metro International Biotech, LLC, Worcester, MA (US)

(72) Inventors: Matthew Baevsky, Worcester, MA (US); Karen Lavery, Worcester, MA (US); Jonathan N. Kremsky, Worcester, MA (US); James M. McKearin, Worcester, MA (US)

(73) Assignee: Metro International Biotech, LLC, Worcester, MA (US)

( * ) Notice: Subject to any disclaimer, the term of this patent is extended or adjusted under 35 U.S.C. 154(b) by 831 days.

(21) Appl. No.: 17/633,693

(22) PCT Filed: Aug. 13, 2020

(86) PCT No.: PCT/US2020/046110

§ 371 (c)(1),
(2) Date: Feb. 8, 2022

(87) PCT Pub. No.: WO2021/030551

PCT Pub. Date: Feb. 18, 2021

(65) Prior Publication Data

US 2022/0324899 A1 Oct. 13, 2022

Related U.S. Application Data

(60) Provisional application No. 62/889,376, filed on Aug. 20, 2019, provisional application No. 62/886,869, filed on Aug. 14, 2019.

(51) Int. Cl.

| | |
|---|---|
| ***C07H 19/048*** | (2006.01) |
| ***A61K 31/706*** | (2006.01) |
| ***A61P 1/16*** | (2006.01) |
| ***A61P 35/00*** | (2006.01) |

(52) U.S. Cl.
CPC ......... *C07H 19/048* (2013.01); *A61K 31/706* (2013.01); *A61P 1/16* (2018.01); *A61P 35/00* (2018.01)

(58) Field of Classification Search
CPC ....... C07H 19/048; A61K 31/706; A61P 1/16; A61P 35/00
See application file for complete search history.

(56) References Cited

U.S. PATENT DOCUMENTS

| | | | | |
|---|---|---|---|---|
| 4,361,572 | A | 11/1982 | Takaku et al. | |
| 2012/0022013 | A1 | 1/2012 | Sinclair et al. | |
| 2017/0189433 | A1 | 7/2017 | Szczepankiewicz et al. | |
| 2017/0325459 | A1 | 11/2017 | Bretschneider et al. | |
| 2018/0162834 | A1 | 6/2018 | Lee et al. | |
| 2018/0186824 | A1 | 7/2018 | Migaud et al. | |
| 2018/0258127 | A1 | 9/2018 | Migaud et al. | |
| 2021/0371446 | A1* | 12/2021 | Sinclair ................ | C07H 19/048 |

FOREIGN PATENT DOCUMENTS

| | | | | |
|---|---|---|---|---|
| EP | 3369738 | A1 | 9/2018 | |
| EP | 3431472 | A2 * | 1/2019 | ............. A23L 33/10 |
| EP | 4013766 | B1 | 1/2025 | |
| WO | WO-2007/061798 | A2 | 5/2007 | |
| WO | WO-2015/014722 | A1 | 2/2015 | |
| WO | WO-2015/186114 | A1 | 12/2015 | |
| WO | WO-2017/160116 | A9 | 11/2017 | |
| WO | WO-2020/081654 | A1 | 4/2020 | |
| WO | WO-2021/030551 | A1 | 2/2021 | |

OTHER PUBLICATIONS

Oh et al. (Chem Bio Chem, 2014, vol. 15, pp. 1121-1130). (Year: 2014).*
WO2017160116A9 English translation by Translations Service Center, United States Patent and Trademark Office Jan. 14, 2025 (Year: 2017).*
Lee, J.; et al. “Selective Cytotoxicity of the NAMPT Inhibitor FK866 Toward Gastric Cancer Cells With Markers of the Epithelial-Mesenchymal Transition, Due to Loss of NAPRT”, Gastroenterology 2018, vol. 155, pp. 799-814. (Year: 2018).*
Hara, N.; et al. “Elevation of Cellular NAD Levels by Nicotinic Acid and Involvement of Nicotinic Acid Phosphoribosyltransferase in Human Cells”, The Journal of Biological Chemistry 2007, vol. 282, pp. 24574-24582. (Year: 2007).*
Galli et al., “Medicinal Chemistry of Nicotinamide Phosphoribosyltransferase (NAMPT) Inhibitors,” Journal of Medicinal Chemistry, 56(16):6279-6296 (2013).
International Search Report and Written Opinion for International Application No. PCT/US2020/03225 mailed Jan. 13, 2021.
Kang et al., “Crystal Structure of Rattus norvegicus Visfatin/PBEF/Nampt in Complex with an FK866-Based Inhibitor,” Mol. Cells, 27:667-671 (2009).
Nozaki et al., Medicinal Chemistry, 1st edition, Kagakudojin Co., Ltd., 1995, pp. 98-99(English translation included).
Wermuth, “Molecular Transformation Based on Equivalent Substitution,” Chapter 13 in Latest Medicinal Chemistry (saishin soyaku-kagaku), the first volume, Technomics INC. Aug. 15, 1998, pp. 235-271.
Extended European Search Report for EP Application No. 20852455.3 dated Aug. 14, 2023.

(Continued)

*Primary Examiner* — Andrea Olson
*Assistant Examiner* — Benjamin M Brandsen
(74) *Attorney, Agent, or Firm* — Foley Hoag LLP; David P. Halstead; Tesia V. Chciuk

(57) ABSTRACT

The invention relates to compounds and compositions for modulation of nicotinamide adenine dinucleotide (NAD+). The invention also relates to methods of making such compounds and compositions. The invention relates to pharmaceutical compositions containing one or more NAD+ modulating compounds as a first ingredient in combination with one or more active pharmaceutical ingredients. Further, the invention relates to methods of using such compounds or compositions to promote the increase of intracellular levels of nicotinamide adenine dinucleotide (NAD+) in cells and tissues for treating diseases and/or improving cell and tissue survival.

12 Claims, 5 Drawing Sheets

(56) References Cited

OTHER PUBLICATIONS

Kadam et al., "Structure Function Analysis of Leishmania Sirtuin: An Ensemble of In Silico and Biochemical Studies", Chemical Biology & Drug Design, , vol. 71, No. 5, pp. 501-506, (2008).
Ruf et al., "Novel nicotinamide analog as inhibitor of nicotinamide N-methyltransferase", Bioorganic & Medicinal Chemistry Letters, vol. 28, No. 5, pp. 922-925, (2018).
Pencina et al., "Nicotinamide Adenine Dinucleotide Augmentation in Overweight or Obese Middle-Aged and Older Adults: A Physiologic Study", The Journal of Clinical Endocrinology & Metabolism, Feb. 6, 2023, 00, pp. 1-13.
Pencina et al., "MIB-626, an Oral Formulation of a Microcrystalline Unique Polymorph of Beta-Nicotinamide Mononucleotide, Increases Circulating Nicotinamide Adenine Dinucleotide and its Metabolome in Middle-Aged and Older Adults", J Gerontol A Biol Sci Med Sci, 2023, vol. 78, No. 1, 90-96.

* cited by examiner

COMPOUNDS AND COMPOSITIONS FOR DIFFERENTIAL MODULATION OF NICOTINAMIDE ADENINE DINUCLEOTIDE

RELATED APPLICATIONS

This application is the U.S. national phase of International Application No. PCT/US2020/046110, filed Aug. 13, 2020, which claims priority to U.S. Provisional Application No. 62/886,869, filed Aug. 14, 2019, and U.S. Provisional Application No. 62/889,376, filed Aug. 20, 2019, each of which is incorporated herein by reference in its entirety.

BACKGROUND

Nicotinamide adenine dinucleotide (NAD) and related naturally-occurring compounds are known as essential coenzymes in cellular redox reactions in all living organisms. Several lines of evidence have shown that NAD participates in a number of important signaling pathways in mammalian cells, including poly(ADP-ribosyl)ation in DNA repair (Menissier de Murcia et al., EMBO J., (2003) 22, 2255-2263), mono-ADP-ribosylation in the immune response and G protein-coupled signaling (Corda et al., EMBO J., (2003) 22, 1953-8), and the synthesis of cyclic ADP-ribose and nicotinate adenine dinucleotide phosphate (NAADP) in intracellular calcium signaling (Lee, Annu. Rev. Pharmacol. Toxicol., (2001) 41, 317-345). It has also been shown that NAD and its metabolites play an important role in transcriptional regulation (Lin et al., Cuff. Opin. Cell. Biol., (2003) 15, 241-246). In particular, the discovery of Sir2 NAD-dependent deacetylase activity (e.g., Imai et al., Nature, (2000) 403, 795-800; Landry et al., Biochem. Biophys. Res. Commun., (2000) 278, 685-690; Smith et al., Proc. Natl. Acad. Sci. USA, (2000) 97, 6658-6663) drew attention to this role of NAD. Nicotinamide phosphoribosyltransferase (NAMPT) plays a role in the salvage pathway for NAD+ synthesis, and the compound FK866 is a small molecule inhibitor of NAMPT (Kang et al, Mol. Cells, 27, 667-671, 2009; Galli et al., J. Med. Chem. 2013, 56, 16, 6279-6296). Various other NAMPT inhibitors have been reported (e.g., Industry-Academic Cooperation Foundation, Yonsei University, EP 3 431 472 A2).

Despite the advances in understanding the biology of NAD, there remains a need for improved compositions and methods of using such compositions for pharmacologic intervention and/or controlled modulation of the NAD pathway in living cells and tissues, including modulations of the NAD pathway that are not possible with naturally-occurring compounds.

SUMMARY

The invention relates to compounds and compositions for modulation of nicotinamide adenine dinucleotide (NAD, also referred to as NAD+ in its oxidized form and NADH in its reduced form). In some embodiments, the invention relates to methods of making such compounds and compositions. In some embodiments, the invention relates to pharmaceutical compositions containing one or more NAD-modulating compounds as an active pharmaceutical ingredient alone or in combination with one or more other active pharmaceutical ingredients. In further embodiments, the invention relates to methods of using such compounds or compositions to promote the increase of intracellular levels of nicotinamide adenine dinucleotide (NAD) in cells and tissues for treating diseases and/or improving cell and tissue survival. Methods of using such compounds or compositions include administration of such compounds and compositions to promote the increase or maintenance of intracellular levels of nicotinamide adenine dinucleotide (NAD) in healthy cells and tissues thus improving or protecting healthy cell and tissue survival. Also included are methods of increasing or maintaining intracellular levels of NAD in selected cells or tissues while simultaneously reducing NAD levels in unhealthy tissue or cells thus reducing the viability of unhealthy cells and tissue. In certain embodiments, the invention relates to methods of using such compounds or compositions to decrease the viability of unhealthy cells and tissue to a greater degree than any reduction in viability of healthy cells and tissue via a differential decrease in intracellular levels of NAD.

DETAILED DESCRIPTION

Definitions

Figure 1A:
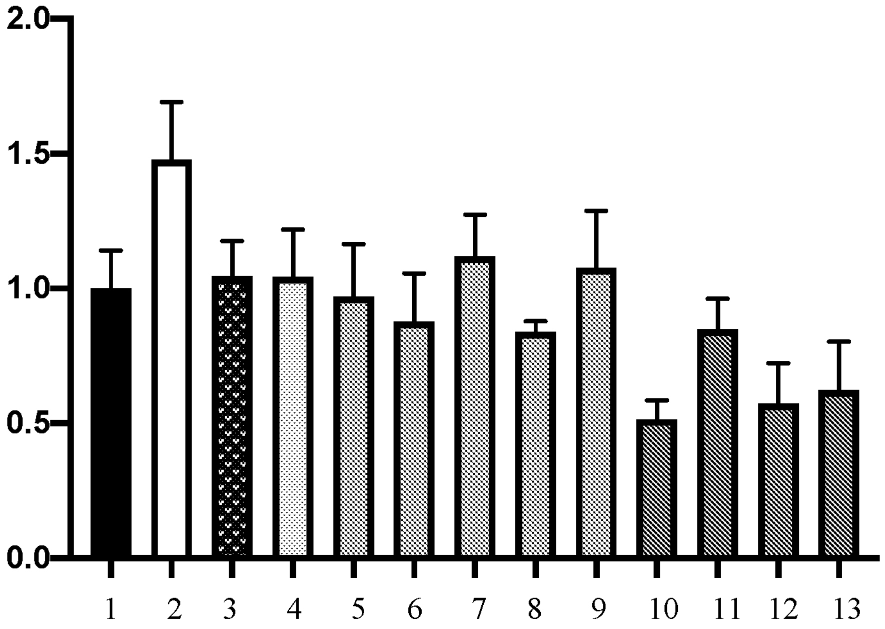
FIG. 1A and FIG. 1B depict NAD(H) in cells upon treatment with control or compounds according to Formula 1.

Unless defined otherwise, all technical and scientific terms used herein have the meaning commonly understood by a person skilled in the art of the present disclosure. As used herein, the following terms have the meanings ascribed to them below, unless specified otherwise.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The phrase "a" or "an" entity as used herein refers to one or more of that entity; for example, a compound refers to one or more compounds or at least one compound. As such, the terms "a" (or "an"), "one or more", and "at least one" can be used interchangeably herein.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds.

Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-tirfluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

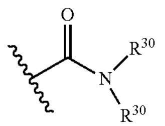

wherein each $R^{30}$ independently represents a hydrogen or hydrocarbyl group, or two $R^{30}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

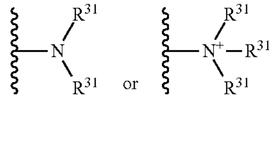

wherein each $R^{31}$ independently represents a hydrogen or a hydrocarbyl group, or two $R^{31}$ are taken together with the N atom to which they are attached complete a heterocycle having from 4 to 8 atoms in the ring structure. The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably, the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

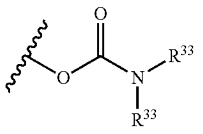
or
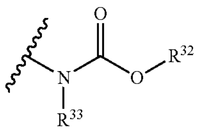

wherein $R^{32}$ and $R^{33}$ independently represent hydrogen or a hydrocarbyl group, such as an alkyl group, or $R^{32}$ and $R^{33}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond.

The term "carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group $—OCO_2—R^{34}$, wherein $R^{34}$ represents a hydrocarbyl group.

The term "carboxy", as used herein, refers to a group represented by the formula $—CO_2H$.

The term "ester", as used herein, refers to a group $—C(O)OR^{35}$ wherein $R^{35}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical.

Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group $-OSO_3H$, or a pharmaceutically acceptable salt thereof.

The term "sulfonamide" is art-recognized and refers to the group represented by the general formulae

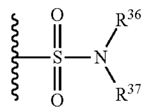

or

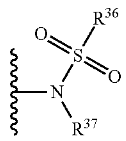

wherein $R^{36}$ and $R^{37}$ independently represent hydrogen or hydrocarbyl, such as alkyl, or $R^{36}$ and $R^{37}$ taken together with the intervening atom(s) complete a heterocycle having from 4 to 8 atoms in the ring structure.

The term "sulfoxide" is art-recognized and refers to the group $-S(O)-R^{38}$, wherein $R^{38}$ represents a hydrocarbyl.

The term "sulfonate" is art-recognized and refers to the group $SO_3H$, or a pharmaceutically acceptable salt thereof.

The term "sulfone" is art-recognized and refers to the group $-S(O)_2-R^{39}$, wherein $R^{39}$ represents a hydrocarbyl.

The term "thioalkyl", as used herein, refers to an alkyl group substituted with a thiol group.

The term "thioester", as used herein, refers to a group $-C(O)SR^{40}$ or $-SC(O)R^{40}$ wherein $R^{40}$ represents a hydrocarbyl.

The term "thioether", as used herein, is equivalent to an ether, wherein the oxygen is replaced with a sulfur.

The term "protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3rd Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

In certain embodiments, compounds of the invention may be racemic. In certain embodiments, compounds of the invention may be enriched in one enantiomer. For example, a compound of the invention may have greater than about 30% ee, about 40% ee, about 50% ee, about 60% ee, about 70% ee, about 80% ee, about 90% ee, or even about 95% or greater ee. In certain embodiments, compounds of the invention may have more than one stereocenter. In certain such embodiments, compounds of the invention may be enriched in one or more diastereomer. For example, a compound of the invention may have greater than about 30% de, about 40% de, about 50% de, about 60% de, about 70% de, about 80% de, about 90% de, or even about 95% or greater de.

In certain embodiments, the therapeutic preparation may be enriched to provide predominantly one enantiomer of a compound (e.g., of Formula (1)). An enantiomerically enriched mixture may comprise, for example, at least about 60 mol percent of one enantiomer, or more preferably at least about 75, about 90, about 95, or even about 99 mol percent. In certain embodiments, the compound enriched in one enantiomer is substantially free of the other enantiomer, wherein substantially free means that the substance in question makes up less than about 10%, or less than about 5%, or less than about 4%, or less than about 3%, or less than about 2%, or less than about 1% as compared to the amount of the other enantiomer, e.g., in the composition or compound mixture. For example, if a composition or compound mixture contains about 98 grams of a first enantiomer and about 2 grams of a second enantiomer, it would be said to contain about 98 mol percent of the first enantiomer and only about 2% of the second enantiomer.

In certain embodiments, the therapeutic preparation may be enriched to provide predominantly one diastereomer of a compound (e.g., of Formula (1)). A diastereomerically enriched mixture may comprise, for example, at least about 60 mol percent of one diastereomer, or more preferably at least about 75, about 90, about 95, or even about 99 mol percent.

The terms "optional" or "optionally" as used herein means that a subsequently described event or circumstance may but need not occur, and that the description includes instances where the event or circumstance occurs and instances in which it does not. For example, "optional bond" means that the bond may or may not be present, and that the description includes single, double, or triple bonds.

The term "purified," as described herein, refers to the purity of a given compound. For example, a compound is "purified" when the given compound is a major component of the composition, i.e., at least about 50% w/w pure. Thus, "purified" embraces at least about 50% w/w purity, at least about 60% w/w purity, at least about 70% purity, at least about 80% purity, at least about 85% purity, at least about 90% purity, at least about 92% purity, at least about 94% purity, at least about 96% purity, at least about 97% purity, at least about 98% purity, at least about 99% purity, at least about 99.5% purity, and at least about 99.9% purity, wherein "substantially pure" embraces at least about 97% purity, at least about 98% purity, at least about 99% purity, at least about 99.5% purity, and at least about 99.9% purity.

The term "salts," as described herein, refers to a compound comprising a cation and an anion, which can be produced by the protonation of a proton-accepting moiety and/or deprotonation of a proton-donating moiety. It should be noted that protonation of the proton-accepting moiety results in the formation of a cationic species in which the charge is balanced by the presence of a physiological anion, whereas deprotonation of the proton-donating moiety results in the formation of an anionic species in which the charge is balanced by the presence of a physiological cation. In its broadest sense, the term "salts" includes zwitterions. In some uses, the term "salts" may be limited to pairs of anions and cations that are not covalently linked.

The phrase "pharmaceutically acceptable salt" means a salt that is pharmaceutically acceptable. Examples of pharmaceutically acceptable salts include, but are not limited to: (1) acid addition salts, formed with inorganic acids such as hydrochloric acid, hydrobromic acid, sulfuric acid, nitric acid, phosphoric acid, and the like; or formed with organic acids such as glycolic acid, pyruvic acid, lactic acid, malonic acid, malic acid, maleic acid, fumaric acid, tartaric acid, citric acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, lauryl sulfuric acid, gluconic acid, glutamic acid, salicylic acid, muconic acid, and the like or (2) basic addition salts formed with the conjugate bases of any of the inorganic acids listed above, wherein the conjugate bases comprise a cationic component selected from among $Na^+$, $K^+$, $Mg^{2+}$, $Ca^{2+}$, $NH_gR_{4-g}^+$, in which R is a $C_{1-3}$ alkyl and g is a number selected from 0, 1, 2, 3, or 4. It should be understood that all references to pharmaceutically acceptable salts include solvent addition forms (solvates) or crystal forms (polymorphs) as defined herein, of the same acid addition salt.

The present invention also includes useful forms of the compounds of the present invention, such as metabolites, hydrates, solvates, prodrugs, salts, in particular pharmaceutically acceptable salts, and/or co-precipitates.

The compounds of the present invention can exist as a hydrate, or as a solvate, wherein the compounds of the present invention form a crystal that contains molecules of polar solvents, in particular water, methanol or ethanol, for example, as structural element of the crystal lattice of the compounds. The molecules of polar solvents, in particular water, may be present in a stoichiometric or non-stoichiometric ratio with the molecules of the compound. In the case of stoichiometric solvates, e.g., a hydrate, hemi-, (semi-), mono-, sesqui-, di-, tri-, tetra-, penta- etc. solvates or hydrates, respectively, are possible. The present invention includes all such hydrates or solvates.

Further, it is possible for the compounds of the present invention to exist in free form, e.g., as a free base, or as a free acid, or as a zwitterion, or to exist in the form of a salt. Said salt may be any salt, either an organic or inorganic addition salt, particularly any pharmaceutically acceptable organic or inorganic addition salt, which is customarily used in pharmacy, or which is used, for example, for isolating or purifying the compounds of the present invention.

The term "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys.

The terms "treatment", "treating", "palliating" and "ameliorating" are used interchangeably herein. These terms refer to an approach for obtaining beneficial or desired results including, but not limited to, therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient can still be afflicted with the underlying disorder. For prophylactic benefit, the pharmaceutical compounds and/or compositions can be administered to a patient at risk of developing a particular disease, or to a patient reporting one or more of the physiological symptoms of a disease, even though a diagnosis of this disease may not have been made.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the subject of one or more of the disclosed compositions. If it is administered prior to clinical manifestation of the unwanted condition (e.g., disease or other unwanted state of the subject) then the treatment is prophylactic (i.e., it protects the subject against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "preparation" or "dosage form" is intended to include both solid and liquid formulations of the active compound and one skilled in the art will appreciate that an active ingredient can exist in different preparations depending on the desired dose and pharmacokinetic parameters.

The term "excipient" as used herein refers to a compound that is used to prepare a pharmaceutical composition, and is generally safe, non-toxic and neither biologically nor otherwise undesirable, and includes excipients that are acceptable for veterinary use as well as human pharmaceutical use.

The term "greater than zero" refers to an amount that is at the lower limit of detection by any quantitative means known in the art. Non-limiting examples of methods for quantifying a chemical substance include chromatography (liquid LC, high-performance liquid HPLC, gas G), electrospray ionization (ESI), atmospheric pressure chemical ionization (APCI), and atmospheric pressure photoionization (APPI). These separation methods are coupled to a mass analyzer that identifies the compound being measured. Mass spectrometry techniques include triple quadrupole (QQQ), ion trap (IT), triple quadrupole-linear ion traps (QTrap), time of flight (TOF), triple quadrupole-time of flight (Q-TOF), Orbitrap, and Fourier transform-ion cyclotron resonance (FT-ICR). See, for example, Roskar, R. et al. *Analytical Methods for Quantification of Drug Metabolites in Biological Samples* 2012, pgs. 87-91.

The phrase "pharmaceutically acceptable" is employed herein to refer to those compounds, materials, compositions, and/or dosage forms which are, within the scope of sound medical judgment, suitable for use in contact with the tissues of a subject without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the subject.

The recitation of a listing of elements in any definition of a variable herein includes definitions of that variable as any single element or combination (or sub-combination) of listed elements. The recitation of an embodiment herein includes that embodiment as any single embodiment or in combination with any other embodiments or portions thereof.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

INCORPORATION BY REFERENCE

All US patents and US and PCT published patent applications and non-patent literature mentioned in this specification are herein incorporated by reference to the same extent as if each independent patent and publication was specifically and individually indicated to be incorporated by reference.

Compounds

Provided herein are compounds having the structure of Formulas 1-2c as shown below.

Formula 1

1

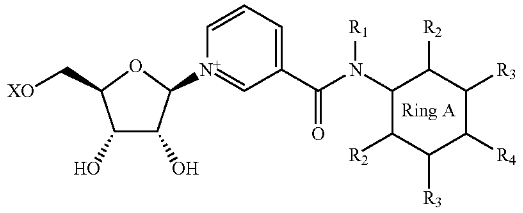

and/or one or more salts thereof, wherein Ring A is a carbocycle or heterocycle, and said carbocycle or heterocycle is aromatic; and X is H or a phosphate group;

$R_1$ is selected from H, a $C_1$-$C_6$ alkyl group, a substituted or unsubstituted carbocycle when taken together with $R_2$ wherein said carbocycle may be aromatic or non-aromatic, and a substituted or unsubstituted heterocycle when taken together with $R_2$ wherein said heterocycle may be aromatic or non-aromatic;

each $R_2$ is independently selected from H, a halogen, a substituted or unsubstituted $C_1$-$C_6$ alkyl group, a substituted or unsubstituted $C_1$-$C_6$ alkenyl group, a substituted or unsubstituted $C_1$-$C_6$ alkynyl group, a substituted or unsubstituted $C_1$-$C_6$ alkoxy group, a carboxylic acid, a substituted or unsubstituted $C_1$-$C_6$ carboxy ester, and a substituted or unsubstituted heterocycle when taken together with $R_1$ wherein said heterocycle may be aromatic or non-aromatic;

each $R_3$ is independently selected from H, a halogen, a substituted or unsubstituted $C_1$-$C_6$ alkyl group, a substituted or unsubstituted $C_1$-$C_6$ alkenyl group, a substituted or unsubstituted $C_1$-$C_6$ alkynyl group, a substituted or unsubstituted $C_1$-$C_6$ alkoxy group, a carboxylic acid, a substituted or unsubstituted $C_1$-$C_6$ carboxy ester, a substituted or unsubstituted carboxamide, a substituted or unsubstituted carbocycle when taken together with $R_4$ wherein said carbocycle may be aromatic or non-aromatic, and a substituted or unsubstituted heterocycle when taken together with $R_4$ wherein said heterocycle may be aromatic or non-aromatic; and $R_4$ is selected from H, a halogen, a substituted or unsubstituted $C_1$-$C_6$ alkyl group, a substituted or unsubstituted $C_1$-$C_6$ alkenyl group, a substituted or unsubstituted $C_1$-$C_6$ alkynyl group, a substituted or unsubstituted $C_1$-$C_6$ alkoxy group, a carboxylic acid, a substituted or unsubstituted $C_1$-$C_6$ carboxy ester, a substituted or unsubstituted carboxamide, a cyano group, a substituted or unsubstituted sulfamoyl group, a substituted or unsubstituted carbocycle or heterocycle wherein said heterocycle or carbocycle may be aromatic or non-aromatic, a substituted or unsubstituted carbocycle when taken together with $R_3$ wherein said carbocycle may be aromatic or non-aromatic, and a substituted or unsubstituted heterocycle when taken together with $R_3$ wherein said heterocycle may be aromatic or non-aromatic.

In various embodiments, a compound of Formula 1 may be represented by Formula 2:

2

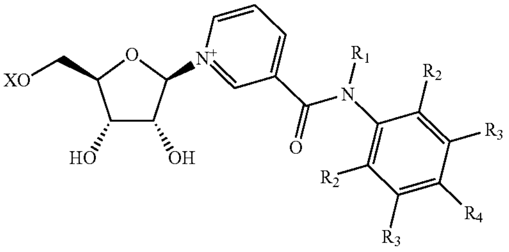

and/or one or more salts thereof, wherein

X is H or a phosphate group;

$R_1$ is H or a $C_1$-$C_6$ alkyl group;

each $R_2$ is independently selected from H, a halogen, a substituted or unsubstituted $C_1$-$C_6$ alkyl group, a substituted or unsubstituted $C_1$-$C_6$ alkenyl group, a substituted or unsubstituted $C_1$-$C_6$ alkynyl group, and a substituted or unsubstituted $C_1$-$C_6$ alkoxy group;

each $R_3$ is independently selected from H, a halogen, a substituted or unsubstituted $C_1$-$C_6$ alkyl group, a substituted or unsubstituted $C_1$-$C_6$ alkenyl group, a substituted or unsubstituted $C_1$-$C_6$ alkynyl group, a substituted or unsubstituted $C_1$-$C_6$ alkoxy group, a carboxylic acid, a substituted or unsubstituted $C_1$-$C_6$ carboxy ester, a substituted or unsubstituted carboxamide, a substituted or unsubstituted carbocycle when taken together with $R_4$ wherein said carbocycle may be aromatic or non-aromatic, and a substituted or unsubstituted heterocycle when taken together with $R_4$ wherein said heterocycle may be aromatic or non-aromatic; and $R_4$ is selected from H, a halogen, a substituted or unsubstituted $C_1$-$C_6$ alkyl group, a substituted or unsubstituted $C_1$-$C_6$ alkenyl group, a substituted or unsubstituted $C_1$-$C_6$ alkynyl group, a substituted or unsubstituted $C_1$-$C_6$ alkoxy group, a carboxylic acid, a substituted or unsubstituted $C_1$-$C_6$ carboxy ester, a substituted or unsubstituted carboxamide, a substituted or unsubstituted carbocycle when taken together with $R_3$ wherein said carbocycle may be aromatic or non-aromatic, and a substituted or unsubstituted heterocycle when taken together with $R_3$ wherein said heterocycle may be aromatic or non-aromatic.

In various embodiments, the compound of Formula 2 has a structure represented by Formula 2a:

2a

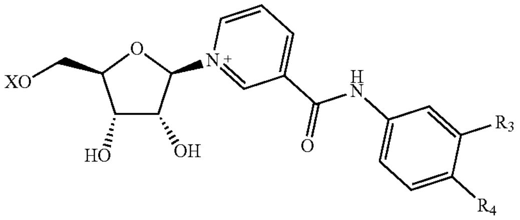

and/or one or more salts thereof, wherein $R_3$ is independently selected from H, a substituted or unsubstituted carbocycle when taken together with $R_4$ wherein said carbocycle may be aromatic or non-aromatic, and a substituted or unsubstituted heterocycle when taken together with $R_4$ wherein said heterocycle may be aromatic or non-aromatic;

$R_4$ is independently selected from H, a halogen, a substituted or unsubstituted $C_1$-$C_6$ alkyl group, a substituted or unsubstituted $C_1$-$C_6$ alkenyl group, a substituted or unsubstituted $C_1$-$C_6$ alkynyl group, a substituted or unsubstituted $C_1$-$C_6$ alkoxy group, a carboxylic acid, a substituted or unsubstituted $C_1$-$C_6$ carboxy ester, a substituted or unsubstituted carboxamide, a substituted or unsubstituted carbocycle when taken together with $R_3$ wherein said carbocycle may be aromatic or non-aromatic, and a substituted or unsubstituted heterocycle when taken together with $R_3$ wherein said heterocycle may be aromatic or non-aromatic;

and further wherein at least one of $R_3$ and $R_4$ is not H.

In various embodiments of Formula 2 and Formula 2a, $R_3$ is H; and $R_4$ is selected from a carboxylic acid, a substituted or unsubstituted $C_1$-$C_6$ carboxy ester, and a substituted or unsubstituted carboxamide. In various embodiments, X is H; and $R_4$ is a carboxymethyl ester group.

Various embodiments include Compounds 1-5, 11, 12, 14, 15, 18, 19, 21, 23, 24, 26, 27, 29, 32, and 35:

1

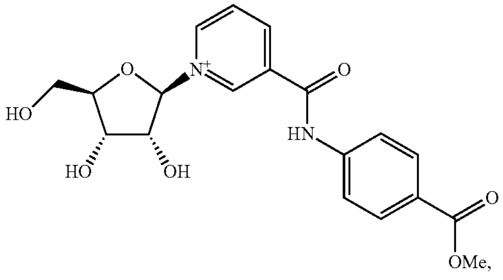

,

-continued
2
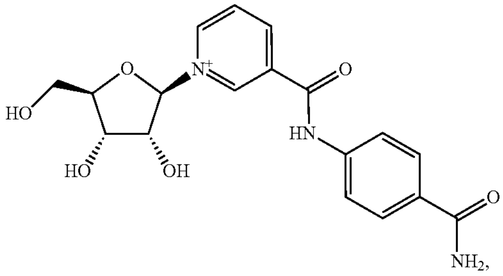
3
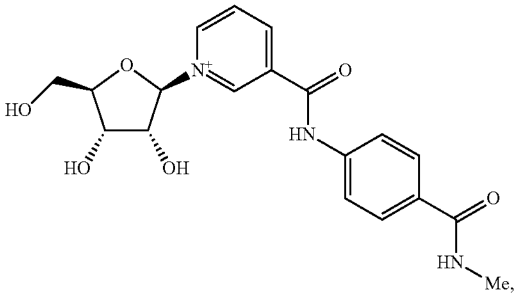
4
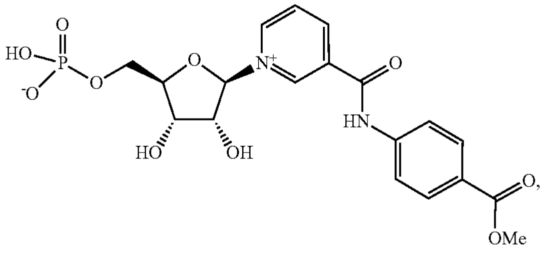
5
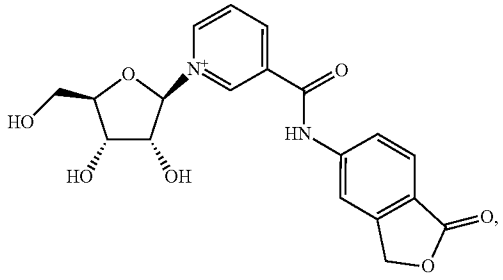
11
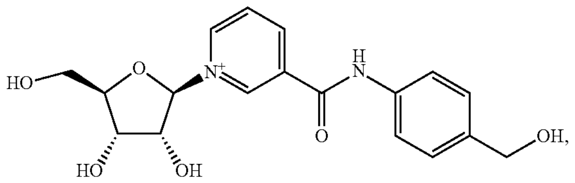
12
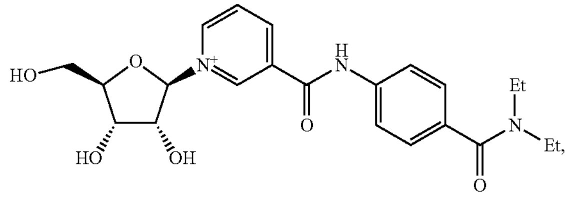
-continued
14
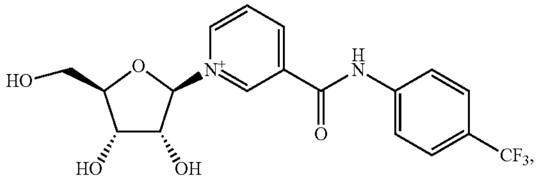
15
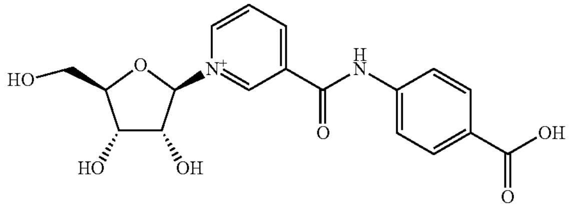
18
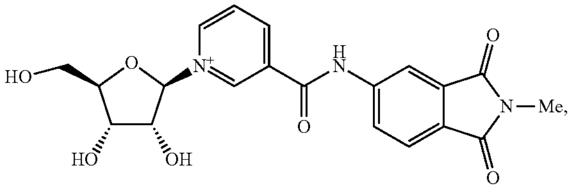
19
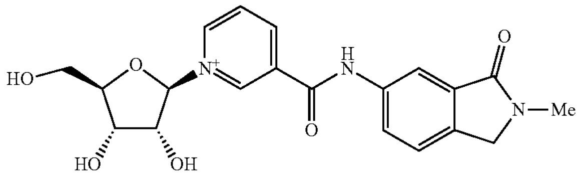
21
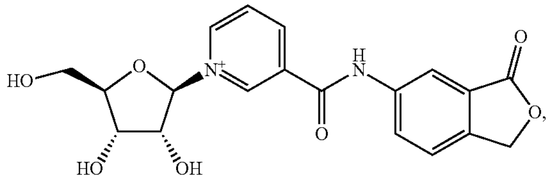
23
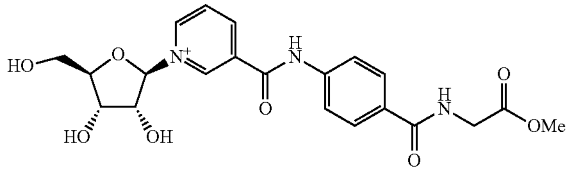
24
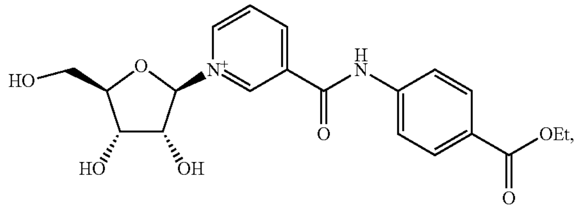

-continued

26

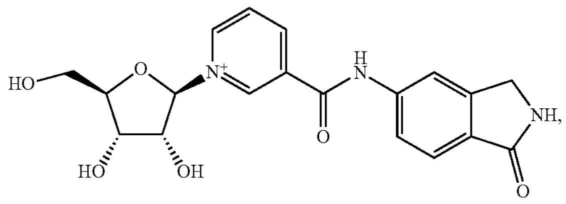

27

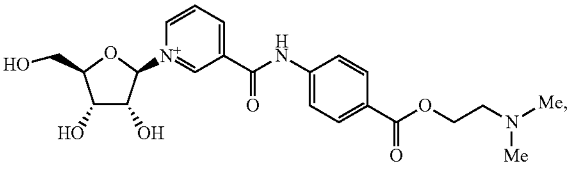

29

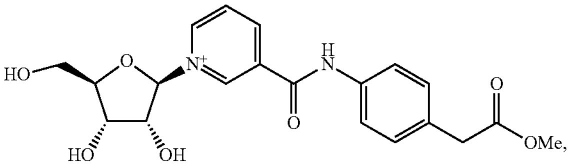

32

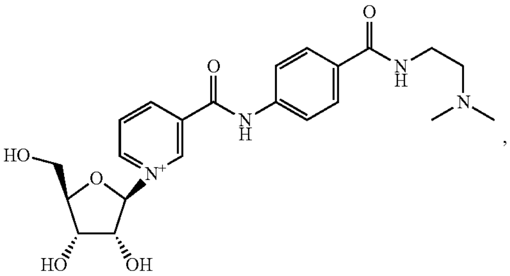

, and

35

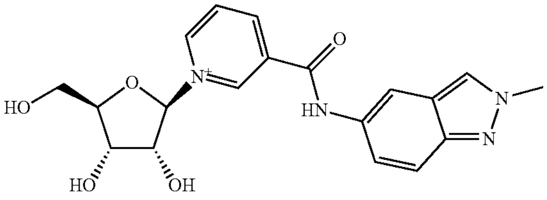

.

In various embodiments, the compound of Formula 2 has a structure represented by Formula 2b:

2b

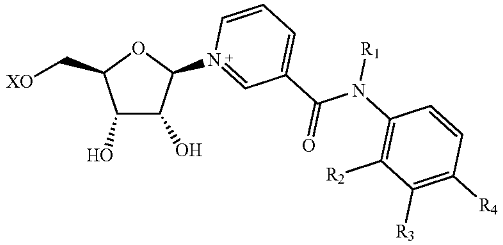

and/or one or more salts thereof, wherein $R_1$ is H or a $C_1$-$C_6$ alkyl group;

$R_2$ is selected from H, and a substituted or unsubstituted $C_1$-$C_6$ alkoxy group;

$R_3$ is H;

and further wherein at least one of $R_1$ and $R^2$ is not H.

In various embodiments of Formula 2 and Formula 2b, $R^1$ is a methyl group. In various embodiments of Formula 2 and Formula 2b, $R^2$ is a methoxy group.

Various embodiments include Compounds 6 and 7:

6

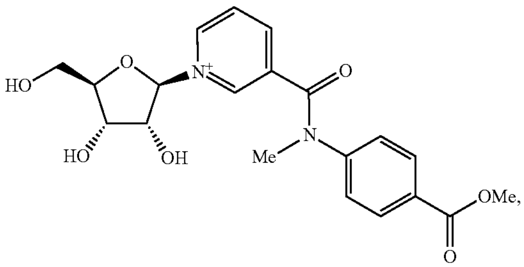

and

7

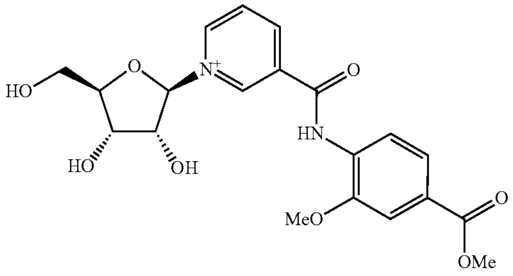

In various embodiments, the compound of Formula 2 has a structure represented by Formula 2c:

2c

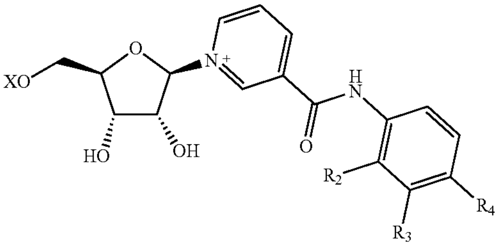

and/or one or more salts thereof, wherein $R_2$ is selected from H, a halogen, a substituted or unsubstituted $C_1$-$C_6$ alkyl group, a substituted or unsubstituted $C_1$-$C_6$ alkenyl group, and a substituted or unsubstituted $C_1$-$C_6$ alkynyl group;

$R_3$ is selected from H, a halogen, a substituted or unsubstituted $C_1$-$C_6$ alkyl group, a substituted or unsubstituted $C_1$-$C_6$ alkenyl group, a substituted or unsubstituted $C_1$-$C_6$ alkynyl group, a substituted or unsubstituted $C_1$-$C_6$ alkoxy group, a carboxylic acid, a substituted or unsubstituted $C_1$-$C_6$ carboxy ester, and a substituted or unsubstituted carboxamide; and $R_4$ is selected from H, a substituted or unsubstituted $C_1$-$C_6$ alkyl group, a substituted or unsubstituted $C_1$-$C_6$ alkenyl group, a substituted or unsubstituted $C_1$-$C_6$ alkynyl group, a substituted or unsubstituted $C_1$-$C_6$ alkoxy group, a carboxylic acid, a substituted or unsubstituted $C_1$-$C_6$ carboxy ester, and a substituted or unsubstituted carboxamide;

and further wherein at least one of $R_2$ and $R_3$ is not H.

In various embodiments of Formula 2 and Formula 2c, $R_2$ is a halogen. In various embodiments of Formula 2 and Formula 2c, $R_3$ is selected from a carboxylic acid, a substituted or unsubstituted $C_1$-$C_6$ carboxy ester, and a substituted or unsubstituted carboxamide.

Various embodiments include Compounds 8, 9, 16, and 20:

8

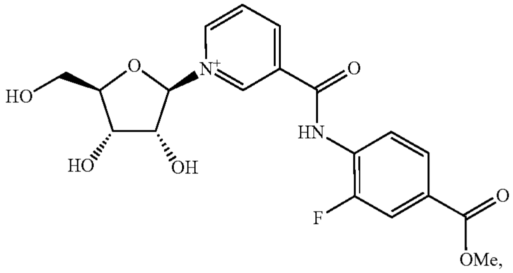

9

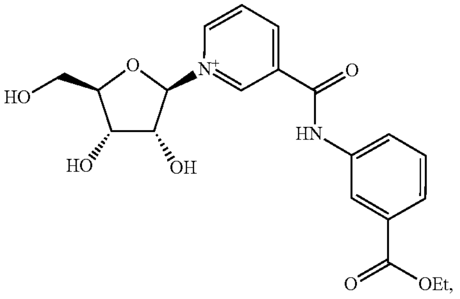

16

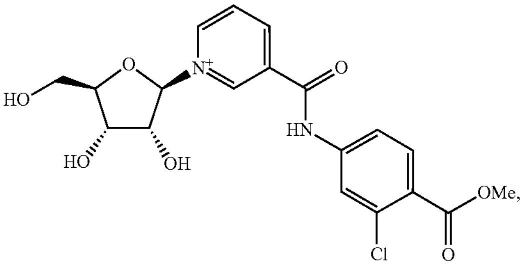

and

20

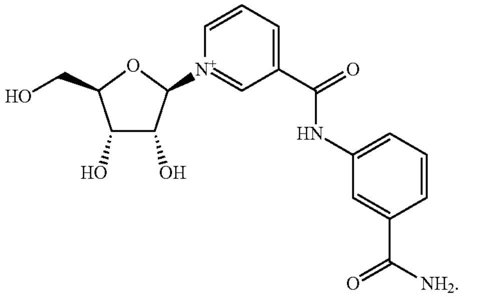

Various embodiments of Formula 1 include Compounds 10, 13, 17, 22, 25, 28, 30, 31, 33, 34, 36, and 37:

10

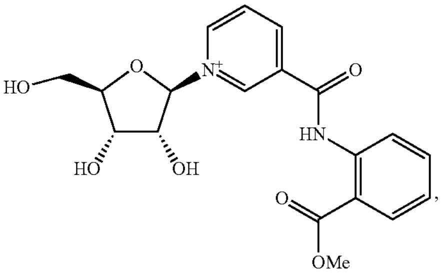

13

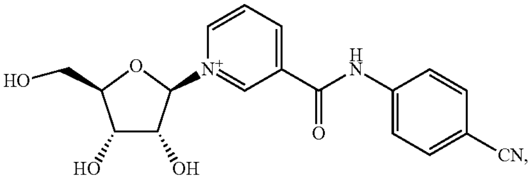

17

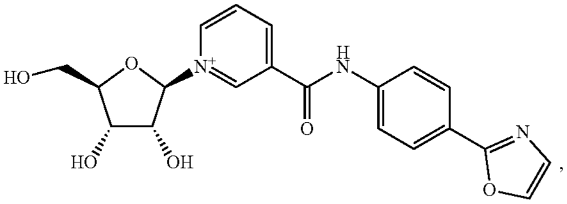

22

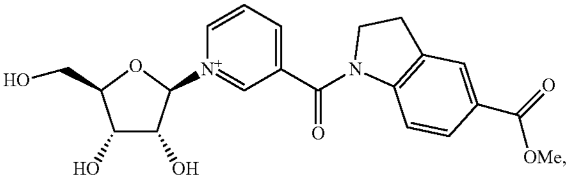

25

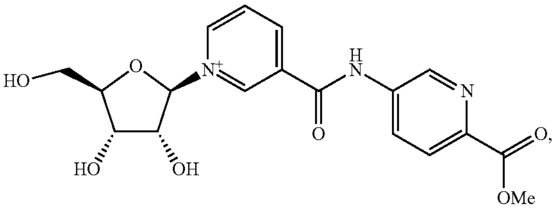

28

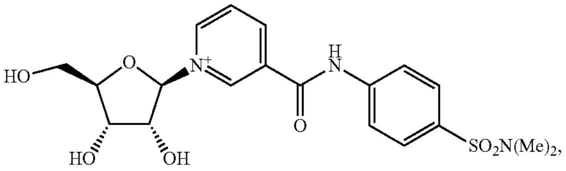

30

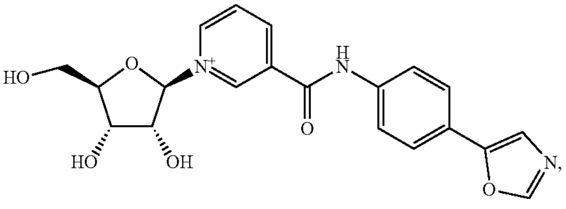

-continued

31

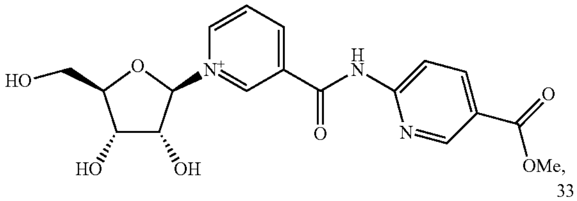

33

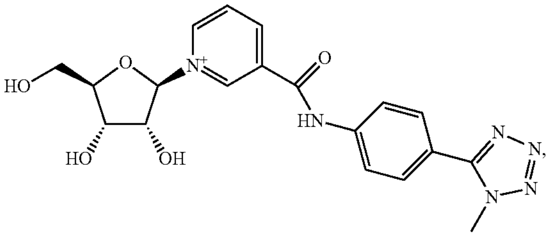

34

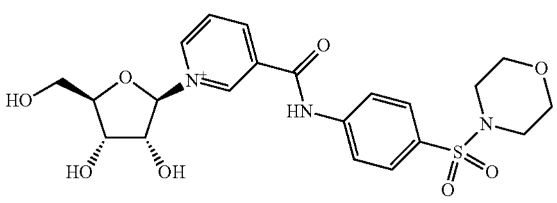

,

36

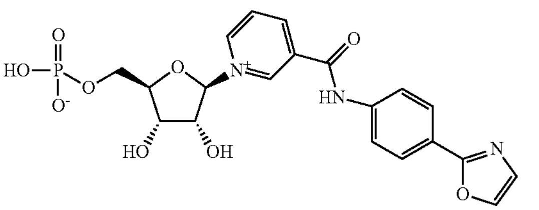

and

37

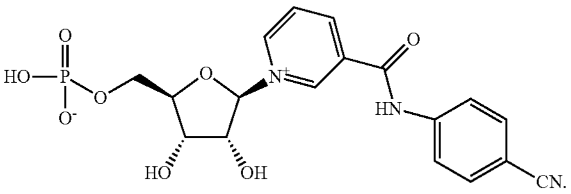

In various embodiments, the compounds of Formula 1 are one or more salts, wherein said salts are formed with a cation selected from $H^+$, $Li^+$, $Na^+$, $K^+$, $Mg^{2+}$, and $Ca^{2+}$ and/or said salts are formed with an anion selected from acetate, trifluoromethansulfonate (triflate), halide, trifluoroacetate, formate, $H_2PO_4^-$, $HPO_4^{2-}$, $OH^-$, $HSO_4^-$, $SO_4^{2-}$, $NO_3^-$, $HCO_3^-$, and $CO_3^{2-}$, and mixtures thereof. In various embodiments, the compound is a zwitterion.

The present invention includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts.

In certain embodiments, the compound is a salt with an anion selected from acetate, triflate, halide, trifluoroacetate, or formate. In other embodiments, if the disclosed compound is in contact with a media, e.g., aqueous media, the anion can be selected from, for example, $OH^-$, $H_2PO_4^-$, $HPO_4^{2-}$, $HSO_4^-$, $SO_4^{2-}$, $NO_3^-$, $HCO_3^-$, and $CO_3^{2-}$.

In some embodiments, the disclosed compounds are in the form of a negatively charged phosphate, which may form a salt with any suitable cation. The cation can alter as the compound is isolated or transferred into media with different anionic species. For example, a disclosed compound may be in the form of a phosphate salt that is a pharmaceutically acceptable salt as described herein. In certain embodiments, the cation can be selected from $Li^+$, $Na^+$, $K^+$, $Mg^{2+}$, and $Ca^{2+}$.

Synthesis

In various embodiments, there is disclosed a method of synthesizing a compound as disclosed herein, comprising reacting an amine-containing precursor with a nicotinic riboside precursor under conditions to condense said precursors to yield a compound according to Formulas 1-2c. In certain embodiments, compounds according the invention can be prepared by the condensation of an appropriate nicotinamide or related precursor with 1,2,3,5-tetraacetyl-β-D-ribofuranose. See, for example, Scheme 1.

In various embodiments, the synthesis can be performed as a one-pot preparation of crude triol with purification of the product by precipitation. In various embodiments, the synthesis can be performed as a one-pot preparation of crude triol and purification of the product by chromatography.

Scheme 1: Preparation of Triols

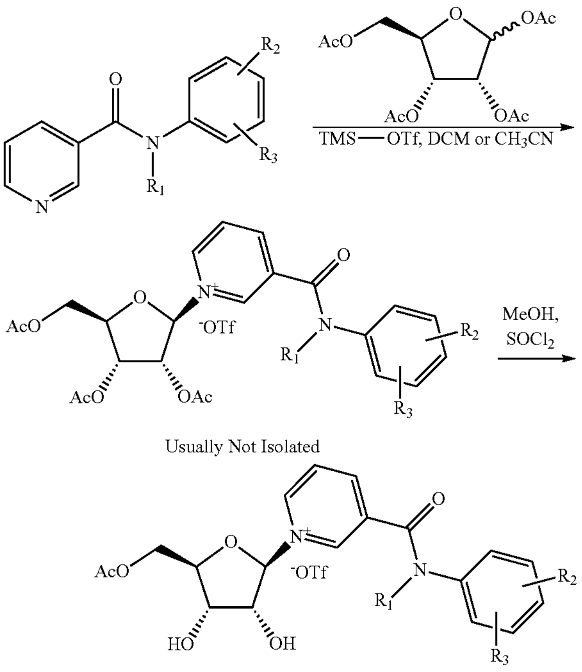

In certain embodiments, the nicotinate starting material can be prepared by condensation of nicotinic acid with, for example an anilide starting material. See, for example, Scheme 2 as an example of amide bond formation in a generic preparation of a nicotinate.

Scheme 2: Preparation of Nicotinates

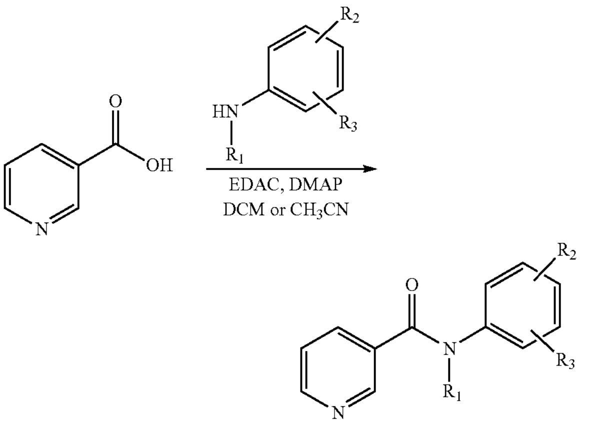

Compositions and Pharmaceutical Formulations

Provided herein are compositions comprising one or more pharmaceutically acceptable excipients and one or more compounds, and/or salts, thereof, wherein the compound has a structure represented by Formulas 1, 2, 2a, 2b, and/or 2c.

Also provided herein are compositions comprising compounds of Formulas 1-2c, including Compounds 1-31. In some embodiments of compositions, the compound is in an amorphous solid form. In other embodiments, the compound is in a crystalline solid form. In some embodiments, the compound is dissolved in a solvent or carrier.

In some embodiments, the pharmaceutically acceptable excipient is selected from an anti-adherent, binder, coating, dye, disintegrant, flavoring agent, glidant, lubricant, preservative, sorbent, sweetener, syrups, elixirs, dispersant, diluent, filler, granulating agent, coating agent, wax, suspending agent, wetting agent, thickener and vehicle and combinations thereof. In some embodiments, the excipient is a solid excipient.

In some embodiments, the pharmaceutically acceptable excipient is present in an amount of at least about 5% by weight, at least about 10% by weight, at least about 15% by weight, at least about 20% by weight, at least about 25% by weight, at least about 30% by weight, at least about 35% by weight, at least about 40% by weight, at least about 45% by weight, at least about 50% by weight, at least about 55% by weight, or at least about 60% by weight of the composition. In some embodiments, the pharmaceutically acceptable excipient is present in an amount of at least about 20% by weight, at least about 25% by weight, at least about 30% by weight, at least about 35% by weight, or at least about 40% by weight, preferably at least about 30% by weight of the composition. In other embodiments, the pharmaceutically acceptable excipient is present in an amount of at least about 50% by weight of the composition.

In some embodiments, the composition is in a solid form selected from a tablet, a pill, a capsule, a caplet, a troche, granules, powders, sachet, dry powder inhalation form, a chewable, a pastille, and a lozenge. In certain embodiments, the composition is in the form of a tablet. In other embodiments, the composition is in a form of a hard or soft gelatin capsule.

The compounds of this invention are formulated with conventional carriers and excipients, which can be selected in accord with ordinary practice. Tablets can contain excipients, glidants, fillers, binders and the like. All formulations will optionally contain excipients such as those set forth in the Handbook of Pharmaceutical Excipients (1986). Suitable excipients are also listed in the US Food and Drug Administration Inactive Ingredients Database. Excipients include ascorbic acid and other antioxidants, chelating agents such as EDTA, carbohydrates such as dextran, hydroxyalkylcellulose, hydroxyalkylmethylcellulose, stearic acid and the like.

While it is possible for active pharmaceutical ingredients to be administered alone, it may be preferable to present them as pharmaceutical formulations. The formulations, both for veterinary and for human use, of the invention comprise at least one active ingredient, as above defined, together with one or more acceptable carriers therefor and optionally other therapeutic ingredients. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Formulations of the present invention suitable for oral administration may be presented as discrete units such as capsules, cachets or tablets, each containing a predetermined amount of the active ingredient as a powder or granules. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Pharmaceutical formulations according to the present invention comprise a compound according to the invention together with one or more pharmaceutically acceptable carriers or excipients and optionally other therapeutic agents. Pharmaceutical formulations containing the active ingredient may be in any form suitable for the intended method of administration. When intended for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques, including microencapsulation, to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active material(s) in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia; and dispersing or wetting agents such as a naturally-occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin. Liquid formulations may also include eye drops or other forms of delivery to the surface of the eye or adjacent locations such as tear ducts. Liquid formulations may include intravenous formulations, excipients, and carriers such as saline solution, or buffered solution, and the packaging or containers for such formulations, for injection or infusion or the like.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The amount of active ingredient that may be combined with the carrier material to produce a single dosage form will vary depending upon the subject treated and the particular mode of administration. For example, a time-release formulation intended for oral administration to humans may contain approximately 1 to approximately 1000 mg of active material compounded with an appropriate and convenient amount of carrier material which may vary from about 5% to about 95% of the total compositions (weight:weight). The pharmaceutical composition can be prepared to provide easily measurable amounts for administration.

Formulations suitable for intrapulmonary or nasal administration have a particle size for example in the range of about 0.1 to about 500 microns, such as about 0.5, about 1, about 30, or about 35 microns etc., which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavoring agents.

In some embodiments, the amount of the compound of Formulas 1-2c in the composition is about 0.001% by weight up to 100% by weight.

In some embodiments, the compound of Formulas 1-2c is the sole active pharmaceutical ingredient in the composition. Alternatively, the compound of Formulas 1-2c is formulated in a composition with one or more additional active pharmaceutical ingredients. When formulated as the sole active pharmaceutical ingredient, the compound of Formulas 1-2c may be administered individually, or as part of a regimen with one or more separately formulated active pharmaceutical ingredients.

When co-administered either in the same formulation or as part of a regimen with one or more separately formulated active pharmaceutical ingredients, the additional active pharmaceutical ingredient may be selected from compounds in the NAD+ pathway, such as nicotinic acid (NA), nicotinamide (Nam), nicotinamide mononucleotide (NMN), nicotinamide riboside (NR), nicotinic acid mononucleotide (NaMN), nicotinic acid riboside (NAR), nicotinamide adenine dinucleotide (NAD+/NADH), nicotinamide adenine dinucleotide phosphate (NADP), and nicotinic acid adenine dinucleotide (NaAD). In some embodiments, the additional active pharmaceutical ingredient is an amorphous solid. In some embodiments, the additional active pharmaceutical ingredient is a crystalline solid. In some embodiments, the additional active pharmaceutical ingredient is amorphous NMN. In some embodiments, the additional active pharmaceutical ingredient is crystalline NMN.

In some embodiments, the additional active pharmaceutical ingredient is a chemotherapeutic agent selected from 1-amino-4-phenylamino-9,10-dioxo-9,10-dihydroanthracene-2-sulfonate (acid blue 25), 1-amino-4-[4-hydroxyphenyl-amino]-9,10-dioxo-9,10-dihydroanthracene-2-sulfonate, 1-amino-4-[4-aminophenylamino]-9,10-dioxo-9,10-dihydroanthracene-2-sulfonate, 1-amino-4-[1-naphthylamino]-9,10-dioxo-9,10-dihydroanthracene-2-sulfonate, 1-amino-4-[4-fluoro-2-carboxyphenylamino]-9,10-dioxo-9,10-dihydroanthracene-2-sulfonate, 1-amino-4-[2-anthracenylamino]-9,10-dioxo-9,10-dihydroanthracene- 2-sulfonate, ABT-263, afatinib dimaleate, axitinib, aminoglutethimide, amsacrine, anastrozole, APCP, asparaginase, AZD5363, *Bacillus* Calmette-Gudrin vaccine (bcg), bicalutamide, bleomycin, bortezomib, β-methylene-ADP (AOPCP), buserelin, busulfan, cabazitaxel, cabozantinib, campothecin, capecitabine, carboplatin, carfilzomib, carmustine, ceritinib, chlorambucil, chloroquine, cisplatin, cladribine, clodronate, cobimetinib, colchicine, crizotinib, cyclophosphamide, cyproterone, cytarabine, dacarbazine, dactinomycin, daunorubicin, demethoxyviridin, dexamethasone, dichloroacetate, dienestrol, diethylstilbestrol, docetaxel, doxorubicin, epirubicin, eribulin, erlotinib, estradiol, estramustine, etoposide, everolimus, exemestane, filgrastim, fludarabine, fludrocortisone, fluorouracil, fluoxymesterone, flutamide, gefitinib, gemcitabine, genistein, goserelin, GSK1120212, hydroxyurea, idarubicin, ifosfamide, imatinib, interferon, irinotecan, ixabepilone, lenalidomide, letrozole, leucovorin, leuprolide, levamisole, lomustine, lonidamine, mechlorethamine, medroxyprogesterone, megestrol, melphalan, mercaptopurine, mesna, metformin, methotrexate, miltefosine, mitomycin, mitotane, mitoxantrone, MK-2206, mutamycin, N-(4-sulfamoylphenylcarbamothioyl) pivalamide, NF279, NF449, nilutamide, nocodazole, octreotide, olaparib, oxaliplatin, paclitaxel, pamidronate, pazopanib, pemexetred, pentostatin, perifosine, PF-04691502, plicamycin, pomalidomide, porfimer, PPADS, procarbazine, quercetin, raltitrexed, ramucirumab, reactive blue 2, rituximab, rolofylline, romidepsin, rucaparib, selumetinib, sirolimus, sodium 2,4-dinitrobenzenesulfonate, sorafenib, streptozocin, sunitinib, suramin, talazoparib, tamoxifen, temozolomide, temsirolimus, teniposide, testosterone, thalidomide, thioguanine, thiotepa, titanocene dichloride, tonapofylline, topotecan, trametinib, trastuzumab, tretinoin, veliparib, vinblastine, vincristine, vindesine, vinorelbine, and vorinostat (SAHA).

In other embodiments, suitable chemotherapeutic agents include: FK866, ABT-263, dexamethasone, 5-fluorouracil, PF-04691502, romidepsin, and vorinostat (SAHA). In other embodiments, chemotherapeutic agents include: 1-amino-4-phenylamino-9,10-dioxo-9,10-dihydroanthracene-2-sulfonate (acid blue 25), 1-amino-4-[4-hydroxyphenylamino]-9,10-dioxo-9,10-dihydroanthracene-2-sulfonate, 1-amino-4-[4-aminophenylamino]-9,10-dioxo-9,10-dihydroanthracene-2-sulfonate, 1-amino-4-[1-naphthylamino]-9,10-dioxo-9,10-dihydroanthracene-2-sulfonate, 1-amino-4-[4-fluoro-2-carboxyphenylamino]-9,10-dioxo-9,10-dihydroanthracene-2-sulfonate, 1-amino-4-[2-anthracenylamino]-9,10-dioxo-9,10-dihydroanthracene-2-sulfonate, APCP, β-methylene-ADP (AOPCP), capecitabine, cladribine, cytarabine, fludarabine, doxorubicin, gemcitabine, N-(4-sulfamoylphenylcarbamothioyl) pivalamide, NF279, NF449, PPADS, quercetin, reactive blue 2, rolofylline sodium 2,4-dinitrobenzenesulfonate, sumarin, and tonapofylline.

Other types of chemotherapeutic agents include immunooncology agents such as abagovomab, adecatumumab, afutuzumab, alemtuzumab, anatumomab mafenatox, apolizumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, obinutuzumab, ocaratuzumab, ofatumumab, olatatumab, pembrolizumab, pidilizumab, rituximab, ticilimumab, samalizumab, and tremelimumab.

In some embodiments, the active pharmaceutical ingredient is selected from PARP inhibitors that are known to repair DNA damage, such as olaparib, veliparib, niraparib, NMS-P118, talazoparib, and rucaparib.

Methods of Treatment, Diseases, Disorders and Conditions

Provided herein are methods of modulating NAD levels in a subject in need thereof, comprising administering a compound, or a salt thereof, wherein the compound is one disclosed herein, and compositions thereof.

Provided herein are methods of treating a disease or disorder associated with NAD biosynthesis, comprising administering a compound, or a salt thereof, wherein the compound is one disclosed herein, and compositions thereof.

Provided herein are methods for using the disclosed compounds and pharmaceutical compositions thereof. The disclosed compounds and pharmaceutical compositions thereof can be useful for a variety of therapeutic applications including, for example, treating and/or reducing a wide variety of diseases and disorders including, for example, diseases or disorders related to aging or stress, diabetes, obesity, neurodegenerative diseases, cardiovascular disease, blood clotting disorders, inflammation, cancer, and/or flushing, etc. The methods comprise administering to a subject in need thereof a disclosed compound and/or pharmaceutical composition thereof. The disclosed compounds and pharmaceutical compositions thereof can be useful for increasing or maintaining NAD levels in certain tissues or cells while decreasing NAD levels in other tissues or cells. In various embodiments, the disclosed compounds and pharmaceutical compositions thereof can be used to selectively decrease NAD levels in some tissues or cells, while decreasing NAD levels to a lesser extent in other tissues or cells.

In certain embodiments, a compound or pharmaceutical composition as disclosed herein may be used for treating or preventing a disease or condition induced or exacerbated by cellular senescence in a subject; methods for decreasing the rate of senescence of a subject, e.g., after onset of senescence; methods for extending the lifespan of a subject; methods for treating or preventing a disease or condition relating to lifespan; methods for treating or preventing a disease or condition relating to the proliferative capacity of cells; and methods for treating or preventing a disease or condition resulting from cell damage or death. In certain embodiments, the method does not act by decreasing the rate of occurrence of diseases that shorten the lifespan of a subject. In certain embodiments, a method does not act by reducing the lethality caused by a disease, such as cancer.

In certain embodiments, a compound or pharmaceutical composition as disclosed herein may be administered to a subject in order to generally increase the lifespan of its cells and to protect its cells against stress and/or against apoptosis. Treating a subject with a compound described herein may be similar to subjecting the subject to hormesis, i.e., mild stress that is beneficial to organisms and may extend their lifespan.

The disclosed compounds and pharmaceutical compositions thereof may be administered to subjects who have recently received or are likely to receive a dose of radiation or toxin. In one embodiment, the dose of radiation or toxin is received as part of a work-related or medical procedure, e.g., working in a nuclear power plant, flying an airplane, an X-ray, CAT scan, or the administration of a radioactive dye for medical imaging; in such an embodiment, the compound is administered as a prophylactic measure. In other embodiments, the radiation or toxin exposure is received unintentionally, e.g., as a result of an industrial accident, habitation in a location of natural radiation, terrorist act, or act of war involving radioactive or toxic material. In such a case, the disclosed compounds and pharmaceutical compositions thereof are preferably administered as soon as possible after the exposure to inhibit apoptosis and the subsequent development of acute radiation syndrome.

In other embodiments, the disclosed compounds and pharmaceutical compositions thereof may be useful for treating age-related disorders, such as, for example, cancer. Exemplary cancers that may be treated using the disclosed compounds and pharmaceutical compositions thereof include those of the brain and kidney; hormone-dependent cancers including breast, prostate, testicular, and ovarian cancers; lymphomas, and leukemias. Other diseases that can be treated include autoimmune diseases, e.g., systemic lupus erythematosus, scleroderma, and arthritis, in which autoimmune cells should be removed. Viral infections such as herpes, HIV, adenovirus, and HTLV-1 associated malignant and benign disorders can also be treated by administration of the disclosed compounds and pharmaceutical compositions thereof.

In some embodiments, the disclosed compounds and pharmaceutical compositions thereof can be used to treat patients suffering from neurodegenerative diseases, and traumatic or mechanical injury to the central nervous system (CNS) or peripheral nervous system (PNS). Examples of neurodegenerative diseases include, but are not limited to, ataxia, Alzheimer's disease (AD), Parkinson's disease (PD), Huntington disease (HD), amyotrophic lateral sclerosis (ALS; Lou Gehrig's disease), diffuse Lewy body disease, chorea-acanthocytosis, primary lateral sclerosis, ocular diseases (ocular neuritis), chemotherapy-induced neuropathies (e.g., from vincristine, paclitaxel, bortezomib), diabetes-induced neuropathies, and Friedreich's ataxia.

Administration of the disclosed compounds and pharmaceutical compositions thereof may increase insulin sensitivity and/or decrease insulin levels in a subject. A subject in need of such a treatment may be a subject who has insulin resistance or other precursor symptom of type II diabetes, who has type II diabetes, or who is likely to develop any of these conditions. For example, the subject may be a subject having insulin resistance, e.g., having high circulating levels of insulin and/or associated conditions, such as hyperlipidemia, dyslipogenesis, hypercholesterolemia, impaired glucose tolerance, high blood glucose sugar level, other manifestations of syndrome X, hypertension, atherosclerosis, and lipodystrophy.

In various embodiments, disclosed herein are methods of differentially modulating nicotinamide adenine dinucleotide (NAD) levels in two or more tissues or cell types. Such methods may comprise administering a compound or composition as disclosed herein, wherein said administering induces a differential response in NAD levels in a first tissue or cell type compared to a second tissue or cell type. In various embodiments, a differential response in NAD levels is selected from at least a 10% difference in NAD levels, at least a 20% difference in NAD levels, at least a 30% difference in NAD levels, at least a 40% difference in NAD levels, at least a 50% difference in NAD levels, at least a 60% difference in NAD levels, at least a 70% difference in NAD levels, at least a 80% difference in NAD levels, at least a 90% difference in NAD levels, at least a 100% difference in NAD levels, at least a 200% difference in NAD levels, at least a 300% difference in NAD levels, at least a 400% difference in NAD levels, at least a 500% difference in NAD levels, at least a 600% difference in NAD levels, at least a 700% difference in NAD levels, at least a 800% difference in NAD levels, at least a 900% difference in NAD levels, and at least a 1000% difference in NAD levels. In various embodiments, a differential response in NAD levels is an increase in NAD levels of at least 10%, 20%, 30%, 40%, 50%, 60%, 70%, 80%, 90%, 100%, 200%, 300%, 400%, 500%, 600%, 700%, 800%, 900%, or 1000% in a first tissue or cell type compared to untreated NAD levels or NAD levels before treatment, and a simultaneous decrease in NAD levels of at least 10%, 20%, 30%, 40%, 50%, 60%, 70%, 80%, 90%, 100%, 200%, 300%, 400%, 500%, 600%, 700%, 800%, 900%, or 1000% in a second tissue or cell type compared to untreated NAD levels or NAD levels before treatment. In various embodiments, a differential response in NAD levels is a maintenance in NAD levels within 10% in said first tissue or cell type compared to untreated NAD levels, and a simultaneous decrease in NAD levels of at least 10%, 20%, 30%, 40%, 50%, 60%, 70%, 80%, 90%, 100%, 200%, 300%, 400%, 500%, 600%, 700%, 800%, 900%, or 1000% in a second tissue or cell type compared to untreated NAD levels. In various embodiments, a differential response in NAD levels is a reduction in NAD levels of at least 10% in a first tissue or cell type compared to untreated NAD levels, and a simultaneous decrease in NAD levels in a second tissue or cell type compared to untreated NAD levels, wherein the decrease in the second tissue or cell type is at least 10%, 20%, 30%, 40%, 50%, 60%, 70%, 80%, 90%, 100%, 200%, 300%, 400%, 500%, 600%, 700%, 800%, 900%, or 1000% more reduction than the reduction in the first tissue or cell type. In various embodiments, the first tissue or cell type is normal tissue or cells, and the second tissue or cell type is neoplastic or cancerous.

Methods of treatment of cancer disclosed herein include treatment of an individual in need thereof. Exemplary cancers that may be treated using the disclosed compounds and pharmaceutical compositions thereof include those of the brain and kidney; hormone-dependent cancers including breast, prostate, testicular, and ovarian cancers; lymphomas, and leukemias. In various embodiments, the cancer may be a common type of cancer in males, such as lung cancer, prostate cancer, colorectal cancer and stomach cancer. In various embodiments, the cancer may be a common type of cancer in females, such as breast cancer, colorectal cancer, lung cancer and cervical cancer. In various embodiments, the cancer may be a skin cancer, such as melanoma, squamous cell carcinoma, or basal cell carcinoma. In various embodiments, the cancer may be a common type of cancer in children, such as acute lymphoblastic leukemia, brain tumors, or non-Hodgkin lymphoma. In various embodiments, the method exhibits a selective cytostatic or cytotoxic effect, wherein the effect is demonstrated by decreased viability of neoplastic or cancerous tissue or cells compared to untreated neoplastic or cancerous tissue or cells.

Methods include the situation where a first tissue or cell type is normal tissue or cells, and the method is a treatment for the promotion of the health or increase in biological activity of the first tissue or cell type in an individual in need thereof. In various embodiments, the treatment does not induce an increase in the risk of a cancer diagnosis in a treated individual. Preferably, the treatment reduces the risk of a cancer diagnosis in an individual receiving treatment.

Various methods include treating or suppressing cancer in an individual in need thereof, where the method comprises administering a compound or composition as described herein. In various embodiments, disclosed herein are methods of increasing or maintaining healthy tissue or cells in an individual in need thereof without increasing the risk of growth of neoplastic or cancerous tissue or cells, such methods comprising administering a compound or composition as described herein.

In various embodiments, described herein are methods of increasing or maintaining healthy tissue or cells in an individual in need thereof while suppressing the growth of neoplastic or cancerous tissue or cells, such methods comprising administering a compound or composition as described herein. In various embodiments, the disclosed methods include methods of increasing or maintaining nicotinamide adenine dinucleotide (NAD) levels in at least one healthy tissue or cell type, such methods comprising administering a compound or composition described herein to the healthy tissue or cell type. In various embodiments, described herein are methods of reducing the viability of at least one cancerous tissue or cell type, such method comprising administering a compound or composition as described herein to the cancerous tissue or cell type.

In addition, methods as described herein include methods of modulating the level of NAD in at least one tissue or cell type in a mixture of tissues or cell types, such methods comprising targeted delivery of a compound or composition as described herein to the desired tissue or cell type. In various embodiments, the targeted delivery is non-systemic.

While the written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the described embodiments, methods, and examples, but by all embodiments and methods within the scope and spirit of the invention.

EXAMPLES

Synthetic Examples

General Procedure A: One-pot preparation of crude triol with purification of the product by precipitation (see Example 1)

General Procedure B: One-pot preparation of crude triol and purification of the product by chromatography (see Example 9)

Example 1: Compound 1

Methyl 4-(1-((2R,3R,4S,5R)-3,4-dihydroxy-5-(hydroxymethyl)tetrahydrofuran-2-yl)-1λ$^4$-pyridine-3-carboxamido)benzoate

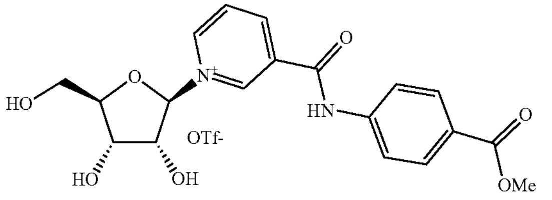 [SMILES: COC(=O)c1ccc(NC(=O)c2ccc[n+]([C@@H]3O[C@H](CO)[C@@H](O)[C@H]3O)c2)cc1]

Trimethylsilyl trifluoromethanesulfonate (TMS-triflate, 4.8 mL, 26.5 mmol, 1.2 eq.) was added dropwise over 5 min. to a stirred mixture of methyl 4-(nicotinamido)benzoate (5.9 g, 23 mmol) and 1,2,3,5-tetraacetyl-β-D-ribofuranose (8.1 g, 25.4 mmol, 1.1 eq.) in dry acetonitrile ($CH_3CN$, 100 mL) under Ar. The reaction mixture was stirred for 1 h at room temperature after which the reaction was determined to be complete after HPLC analysis of an aliquot showed less than 10% of the nicotinamide was present. The reaction mixture was diluted with dry MeOH (50 mL) and concentrated on the rotary evaporator to remove most of the $CH_3CN$. The mixture was diluted with MeOH (100 mL) and cooled in an ice bath. Thionyl chloride ($SOCl_2$, 5.8 mL, 80.5 mmol, 3.5 eq.) was added dropwise and the reaction mixture was stirred for 16 h in the cold room at 5° C. The reaction was determined to be complete after HPLC analysis of an aliquot showed less than 5% of the mono and diacetate intermediates present. The crude product was precipitated by adding the solution to 1.3 L of well-stirred MTBE in a 2 L Erlenmeyer flask. The precipitated solids were filtered and washed with a large volume of MTBE. After drying on the vacuum funnel, the solids were further dried under high vacuum to afford the product (7.7 g, 62%) as a white solid.

$^1$H NMR ($D_2O$): δ 9.64 (s, 1H), 9.28 (d, 1H), 9.04 (d, 1H), 8.29 (dd, 1H), 8.02 (d, 2H), 7.70 (d, 2H), 6.24 (d, 1H), 4.52 (app t, 1H), 4.46 (m, 1H), 4.04 (app dd, 1H), 3.87 (m, 4H or 5H). MS(ESI+) m/z=389.1

Example 2: Compound 2

N-(4-carbamoylphenyl)-1-((2R,3R,4S,5R)-3,4-dihydroxy-5-(hydroxymethyl)tetrahydrofuran-2-yl)-1λ$^4$-pyridine-3-carboxamide

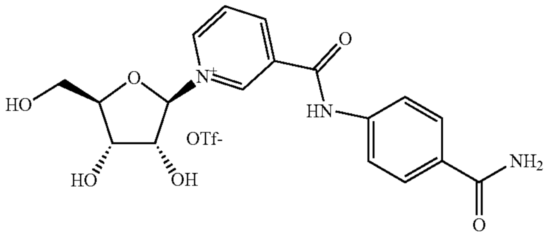 [SMILES: NC(=O)c1ccc(NC(=O)c2ccc[n+]([C@@H]3O[C@H](CO)[C@@H](O)[C@H]3O)c2)cc1]

Following General Procedure A: TMS-triflate (1.2 eq.) was added to a stirred mixture of N-(4-carbamoylphenyl) nicotinamide (1.1 g, 4.6 mmol) and 1,2,3,5-tetraacetyl-β-D-ribofuranose (1.1 eq.) in dry acetonitrile (40 mL). The mixture was stirred at room temperature for 2 h and after removal of the solvent, treated with 3 eq. of $SOCl_2$ in 40 mL of MeOH then stirred at 5° C. for 24 h. The mixture was concentrated to half the original volume and MTBE (50 mL) was slowly added to precipitate the product. The solids were filtered on a sintered glass funnel and washed with 2×10 mL portions of MeOH (pre-cooled to −20° C.) followed by several portions of MTBE. The solids were dried under high vacuum for several hours to furnish the product (1.25 g, 49%) as a white solid.

$^1$H NMR ($D_2O$): δ 9.87 (s, 1H), 9.47 (app d, 1H), 9.17 (app d, 1H), 8.36 (t, 1H), 7.94 (dd, 4H), 6.23 (d, 1H), 4.46 (m, 2H), 4.34 (m, 1H), 3.97 (ab q, 2H). MS(ESI+) m/z=374.1

Example 3: Compound 3

1-((2R,3R,4S,5R)-3,4-dihydroxy-5-(hydroxymethyl)tetrahydrofuran-2-yl)-N-(4-(methylcarbamoyl)phenyl)-1λ[4]-pyridine-3-carboxamide

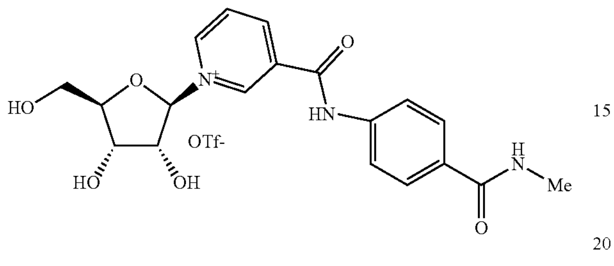

Following General Procedure B: TMS-triflate (1.7 mL, 0.55 mmol, 1.2 eq.) was added to a stirred mixture of N-(4(methylcarbamoyl)phenyl)nicotinamide (1.1 g, 0.46 mmol) and 1,2,3,5-tetraacetyl-β-D-ribofuranose (1.1 eq.) in dry acetonitrile (40 mL) for 2 h. Subsequent workup and treatment with 3 equiv. of $SOCl_2$ in MeOH, followed by stirring at 5° C. for 24 h gave after trituration, the crude product as a semi-solid mass. The material was dissolved in a minimum of 10% MeOH in DCM and loaded onto a 40 g ISCO automated chromatography cartridge. Gradient elution with 5% MeOH in DCM to 30% MeOH in DCM furnished the product (1.1 g, 62%) as a white solid.

$^1$NMR ($D_2O$): δ 11.6 (s, 1H), 9.79 (s, 1H), 9.46 (d, 2H), 9.27 (d, 2H), 8.47 (m, 1H), 8.41 (t, 1H), 7.92 (dd, 4H), 6.25 (d, 1H), 4.40 (t, 1H), 4.27 (m, 1H), 4.18 (t, 1H), 3.79 (ab q, 2H), 2.78 (s, 3H). MS(ESI+) m/z=388.1

Example 4: Compound 4

((2R,3S,4R,5R)-3,4-dihydroxy-5-(3-((4-(methoxycarbonyl)phenyl)carbamoyl)-1λ[4]-pyridin-1-yl)tetrahydrofuran-2-yl)methyl hydrogen phosphate

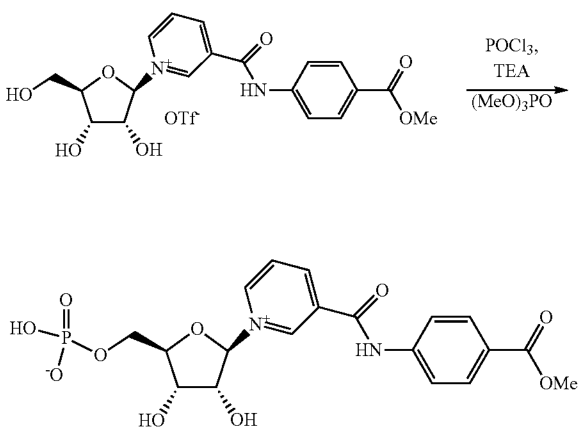

A dry 100 mL flask was charged with 2 g (4.1 mmol) of Compound 1. The flask was flushed with argon and 10 mL of trimethylphosphate was added. The resulting solution was cooled to 0° C. and treated with $POCl_3$ (1.25 g, 8.2 mmol, 2 eq.). The flask was sealed and allowed to stand in the freezer at −10° C. After 2.5 h the homogeneous solution was treated with triethylamine (206 mg, 2.0 mmol) over several minutes and allowed to stand in the freezer overnight. The reaction mixture was cooled in an ice bath and the well-stirred suspension was treated with water (1.5 g, 82 mmol) over several minutes followed solid $NaHCO_3$ (2.4 g, 28.7 mmol) and stirring was continued for 90 min. at 0° C. The reaction mixture was treated with 100 mL of $CH_3CN$ containing 33 mmol of 90% formic acid to produce a white solid. The solid was recovered by filtration, washed with $CH_3CN$ and placed under high vacuum to give the crude product as an off-white solid (3.7 g). This material was purified by medium pressure chromatography on a column containing 50 g of aminopropyl functionalized silica. The product was dissolved in 25 mL of 60%/40% MeOH—$CH_3CN$ containing 100 mM formic acid and the column was equilibrated with the same solvent mixture. The product containing fractions were combined and concentrated; co-evaporated from water (3×25 mL), frozen and lyophilized to give the product (300 mg, 16%) as a white solid.

$^1$H NMR ($D_2O$): δ 9.4 (s, 1H), 9.2 (m, 1H), 8.9 (d, 1H), 8.2 (m, 1H), 7.9 (d, 2H), 7.6 (d, 2H), 6.1 (d, 1H), 4.6 (m, 1H), 4.5 (m, 1H), 4.4 (q, 1H), 4.2 (dq, 1H), 4.1 (dq, 1H), 3.8 (s, 3H). $^{31}$P NMR ($D_2O$): 0.24 ppm. MS(ESI+) m/z=468.1

Example 5: Compound 5

1-((2R,3R,4S,5R)-3,4-dihydroxy-5-(hydroxymethyl)tetrahydrofuran-2-yl)-N-(1-oxo-1,3-dihydroisobenzofuran-5-yl)-1λ[4]-pyridine-3-carboxamide

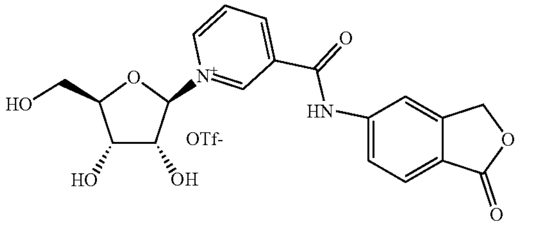 [SMILES: O=C(Nc1ccc2c(c1)COC2=O)c1ccc[n+]([C@@H]2O[C@H](CO)[C@@H](O)[C@H]2O)c1]

Following General Procedure B: TMS-triflate (1.2 eq.) was added to a stirred mixture of N-(1-oxo-1,3-dihydroisobenzofuran-5-yl) nicotinamide (1.2 g, 4.7 mmol) and 1,2,3,5-tetraacetyl-β-D-ribofuranose (1.1 eq.) in dry acetonitrile (40 mL) for 2 h. Evaporation of the solvent and treatment with $SOCl_2$ (3 eq.) in MeOH (40 mL) followed by stirring for 24 h at 5° C. and subsequent workup gave the crude product as a semi-solid mass. The crude product was dissolved a minimum of 5% MeOH in DCM and loaded onto a 24 g ISCO cartridge. Gradient elution with 5% MeOH in DCM to 30% MeOH in DCM furnished the product (1.75 g, 67%) as a white solid.

$^1H$ NMR ($D_2O$): δ 9.63 (s, 1H), 9.26 (d, 1H), 9.04 (d, 1H), 8.28 (t, 1H), 7.86 (s, 1H), 7.75 (d, 1H), 7.59 (d, 1H), 6.23 (d, 1H), 4.52 (t, 1H), 4.44 (m, 1H), 4.34 (t, 1H), 3.95 (ab q, 2H). MS(ESI+) m/z=387.1

Example 6: Compound 6

Methyl 4-(1-((2R,3R,4S,5R)-3,4-dihydroxy-5-(hydroxymethyl)tetrahydrofuran-2-yl)-N-methyl-1λ$^4$-pyridine-3-carboxamido)benzoate

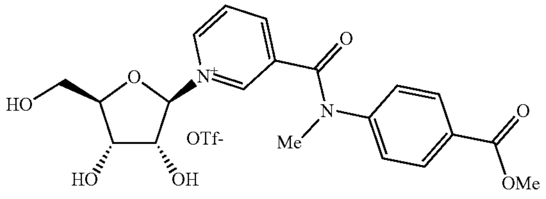 [SMILES: COC(=O)c1ccc(N(C)C(=O)c2ccc[n+]([C@@H]3O[C@H](CO)[C@@H](O)[C@H]3O)c2)cc1]

A dry 100 mL RB was charged with the 3.2 g methyl 4-(N-methylnicotinamido) benzoate (11.8 mmol) and the flask flushed with argon. Under a flow of argon, this was dissolved in 35 mL anhydrous dioxane and treated with 3.8 g of ribose tetraacetate (11.8 mmol). The resulting solution was briefly cooled on ice water and treated with 3.2 g TMS-triflate (14.2 mmol), allowed to warm to ambient temperature and stirred. After 2.5 hours, the reaction proceeded to ~90% completion. The solvent was removed by rotary evaporation and the residue was taken up 50 mL DCM. This was washed with saturated $NaHCO_3$ and brine. The aqueous layer was back-extracted with DCM, the organic layers were combined, and dried over $Na_2SO_4$, filtered and evaporated under high-vacuum to yield 6.9 g of an off-white foam. This was purified on a medium-pressure LC system using a 120 g silica cartridge with a gradient of 0-15% MeOH in DCM. The product fractions were isolated pooled, stripped, and placed on high vac to give the triacetate, 5.6 g (70%).

$^1H$ NMR ($CDCl_3$): δ 9.3 (bd s, 1H); 9.2 (d, 1H); 8.0 (d, 2H); 7.3 (d, 2H); 6.6 (d, 1H); 5.3 (m, 1H); 5.2 (m, 1H); 4.7 (m, 1H); 4.5 (dd, 1H); 4.4 (dd, 1H); 3.9 (s, 3H); 3.6 (s, 3H); 2.2 (s, 3H); 2.1 (s, 3H); 2.0 (s, 3H).

A 250 mL RB was charged with 5.6 g of the above triacetate (8.2 mmol) and the flask flushed with argon. This was dissolved in 75 mL anhydrous MeOH, the resulting solution cooled on ice, and treated dropwise with 2.94 g of $SOCl_2$ (24.7 mmol). The sealed reaction vessel was allowed to stand in the refrigerator at 10° C. After 18 hours, the solvent was removed in vacuo and the residue was triturated with MTBE, then placed on high vacuum to give, 4.7 g as a white solid. This was purified on a 40 g silica ISCO cartridge, using a gradient of 0-15% MeOH in DCM. The product fractions were pooled and stripped to give, 2.5 g as an off-white foam.

$^1H$ NMR ($CDCl_3$): δ 9.0 (d, 1H); 8.1 (d, 1H); 7.8 (m, 3H); 7.2 (d, 2H); 5.8 (d, 1H); 4.2 (m, 2H); 4.1 (d, 2H); 3.8-3.6 (4H); 3.4 (s, 3H); 3.2 (s, 3H).

Example 7: Compound 7

Methyl 4-(1-((2R,3R,4S,5R)-3,4-dihydroxy-5-(hydroxymethyl)tetrahydrofuran-2-yl)-1λ$^4$-pyridine-3-carboxamido)-3-methoxy-benzoate

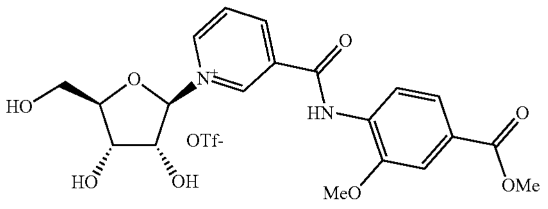 [SMILES: COC(=O)c1ccc(NC(=O)c2ccc[n+]([C@@H]3O[C@H](CO)[C@@H](O)[C@H]3O)c2)c(OC)c1]

Following General Procedure B: TMS-triflate (1.2 eq.) was added to a stirred mixture of methyl 3-methoxy-4-(nicotinamido)benzoate (1.6 g, 5.63 mmol) and 1,2,3,5-tetraacetyl-β-D-ribofuranose (1.1 eq.) in dry acetonitrile (40 mL) and the resultant mixture was stirred for 2 h. Workup as previously described and subsequent treatment with 3 equiv. of $SOCl_2$ in MeOH, followed by stirring at 5° C. for 24 h gave after trituration, the crude product as a semi-solid mass. The crude product was purified using the ISCO (40 g cartridge) eluting with a gradient of DCM to 30% MeOH in DCM to afford the product (715 mg, 23%) as an off-white solid.

$^1H$ NMR ($CD_3OD$): δ 9.84 (s, 1H), 9.67 (d, 1H), 9.12 (d, 1H), 8.31-8.36 (m, 2H), 7.72-7.74 (m, 2H), 6.25 (d, 1H), 4.42-4.52 (m, 2H), 4.36 (m, 1H), 4.04 (s, 3H), 3.96 (ab q, 2H), 3.91 (s, 3H). MS(ESI+) m/z=419.1

Example 8: Compound 8

Methyl 4-(1-((2R,3R,4S,5R)-3,4-dihydroxy-5-(hydroxymethyl)tetrahydrofuran-2-yl)-1λ$^4$-pyridine-3-carboxamido)-3-fluorobenzoate

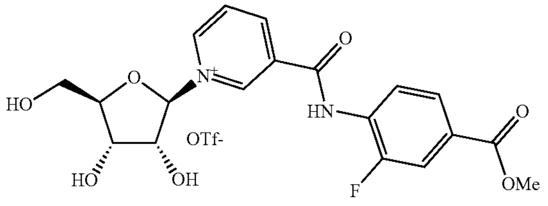 [SMILES: COC(=O)c1ccc(NC(=O)c2ccc[n+]([C@@H]3O[C@H](CO)[C@@H](O)[C@H]3O)c2)c(F)c1]

Following General Procedure B: TMS-triflate (1.2 eq.) was added to a stirred mixture of methyl 3-fluoro-4-(nicotinamido)benzoate (610 mg, 2.31 mmol) and 1,2,3,5-tetraacetyl-β-D-ribofuranose (800 mg, 2.5 mmol, 1.1 eq.) in dry acetonitrile (40 mL) and the mixture was stirred for 2 h at ambient temperature. The solvent was evaporated under reduced pressure and the residue was treated with 3 equiv. of $SOCl_2$ in MeOH, followed by stirring at 5° C. for 24 h. Workup as previously described gave the crude product as a semi-solid mass after removal of excess HCl by co-evaporation with DCM. The crude product was purified on the ISCO (24 g cartridge) eluting with a gradient of DCM to 30% MeOH in DCM to afford the product (400 mg, 31%) as a tan solid.

$^1H$ NMR ($CD_3CN$): δ 9.66 (S, 1H), 9.30 (br s, 1H), 9.26 (d, 1H), 8.98 (d, 1H), 8.26 (t, 2H), 7.93 (d, 1H), 7.87 (d, 1H), 6.14 (d, 1H), 4.47 (t, 1H), 4.13 (m, 1H), 3.94 (ab q, 2H, 3.92 (s, 1H). MS(ESI+) m/z=407.1

Example 9: Compound 9

Ethyl 3-(1-((2R,3R,4S,5R)-3,4-dihydroxy-5-(hydroxymethyl)tetrahydrofuran-2-yl)-1λ$^4$-pyridine-3-carboxamido)benzoate

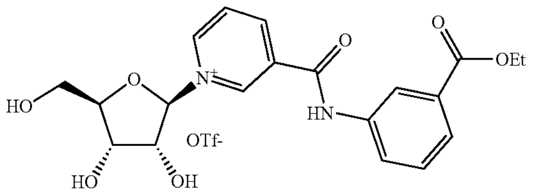 [SMILES: CCOC(=O)c1cccc(NC(=O)c2ccc[n+]([C@@H]3O[C@H](CO)[C@@H](O)[C@H]3O)c2)c1]

TMS-triflate (2.9 mL, 15.7 mmol, 1.2 eq.) was added dropwise to a stirred mixture of ethyl 3-(nicotinamido) benzoate (3.85 g, 14.3 mmol) and 1,2,3,5-tetraacetyl-β-D-ribofuranose (8.1 g, 25.4 mmol, 1.1 eq.) in dry DCM (80 mL) under Ar. The reaction mixture was stirred for 1 h at room temperature, after which the reaction was found to be only 10% complete by HPLC analysis of due to insolubility of the nicotinamide. The reaction mixture was diluted with dry dioxane (30 mL) and additional TMS-triflate (3.0 mL, 1.1 eq.) was added. The reaction mixture was stirred for 1 h and at that time, was found to be complete by HPLC analysis. The mixture was concentrated on the rotary evaporator to approximately 20 mL, diluted with anhydrous absolute EtOH (50 mL), cooled in an ice bath and treated dropwise with $SOCl_2$ (4.2 mL, 57.3 mmol, 4 eq.). The mixture was stirred for 3 days in the cold room at 5° C., then concentrated on the rotary evaporator to approximately 30 mL and triturated with MTBE to precipitate the crude product as a semi-solid mass. The product was further triturated with MTBE to afford an off-white solid (2 g). 1 g of this material was purified on the ISCO Combi Flash® automated chromatography system using a 24 g silica gel cartridge and loading with a minimum of 5% MeOH in DCM. Elution was performed using a gradient of 5% MeOH in DCM to 30% MeOH in DCM. The pure fractions were pooled and concentrated, then co-stripped with DCM to give, after placing under high vacuum for several hours, the pure product (700 mg, 24% overall yield) as a white solid.

$^1$H NMR ($D_2O$): δ 9.64 (s, 1H), 9.30 (d, 1H), 9.04 (d, 1H), 8.42 (s, 1H), 8.27 (app t, 1H), 7.94 (d, 1H), 7.85 (d, 1H), 7.85 (d, 1H), 7.55 (t, 1H), 6.16 (d, 1H), 4.46 (app t, 1H), 4.33-4.43 (m, 2 or 3H), 4.31 (app t, 1H), 3.92 (ab q, 2H), 1.97 (q, 2H). MS(ESI+) m/z=403.1

Example 10: Compound 10

Ethyl 2-(1-((2R,3R,4S,5R)-3,4-dihydroxy-5-(hydroxymethyl)tetrahydrofuran-2-yl)-1λ$^4$-pyridine-3-carboxamido)benzoate

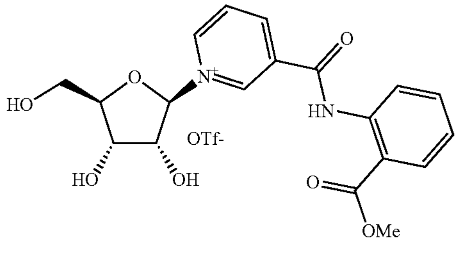 [SMILES: COC(=O)c1ccccc1NC(=O)c1ccc[n+]([C@@H]2O[C@H](CO)[C@@H](O)[C@H]2O)c1]

Trimethylsilyl trifluoromethanesulfonate (TMS-triflate, 3.3 mL, 17.8 mmol, 1.2 eq.) was added dropwise over 5 min. to a stirred mixture of methyl 2-(nicotinamido)benzoate (3.8 g, 14.8 mmol) and 1,2,3,5-tetraacetyl-β-D-ribofuranose (5.2 g, 16.3 mmol, 1.1 eq.) in dry DCM (35 mL) under Ar. The reaction mixture was stirred for 1.5 h at ambient temperature and the reaction was determined to be complete by HPLC. The mixture was cooled in an ice bath, diluted with dry MeOH (50 mL) and thionyl chloride ($SOCl_2$, 3.22 mL, 44.4 mmol, 3 eq.) was added dropwise. The solution was allowed to stand in the cold room at 5° C. for 24 h. The mixture was concentrated to approximately 20 mL on the rotary evaporator and the product was precipitated by the addition of 100 mL of MTBE. After decanting the solution, the residue was twice triturated with MTBE to afford a tan solid. Attempted purification of a 2 g sample by chromatography was not successful leading to decomposition of the product on the column. 1.2 g of the solid was dissolved in anhydrous absolute EtOH (10 mL) and the product was precipitated by the addition of 40 mL of MTBE. After successive trituration with MTBE, the solids were collected by filtration and washed with MTBE. After drying under high vacuum overnight, the product (780 mg) was obtained as an off-white solid with a purity of 95%.

$^1$H NMR (DMSO-$d_6$): δ 11.74 (s, 1H), 9.80 (s, 1H), 9.52 (d, 1H), 9.13 (d, 1H), 8.45 (t, 1H), 8.21 (d, 1H), 8.03 (d, 1H), 7.74 (t, 1H), 7.38 (t, 1H), 6.29 (d, 1H), 4.38 (t, 1H), 4.23 (m, 1H), 3.88 (s, 3H). MS(ESI+) m/z=389.1

Example 11: Compound 11

1-((2R,3R,4S,5R)-3,4-dihydroxy-5-(hydroxymethyl) tetrahydrofuran-2-yl)-N-(4-(hydroxymethyl)phenyl)-1λ$^4$-pyridine-3-carboxamide

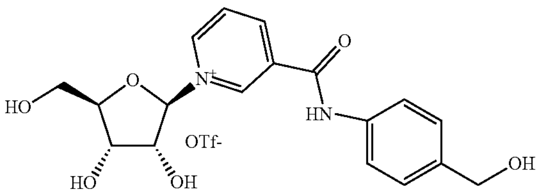 [SMILES: O=C(Nc1ccc(CO)cc1)c1ccc[n+]([C@@H]2O[C@H](CO)[C@@H](O)[C@H]2O)c1]

Following General Procedure B: TMS-triflate (1.2 eq.) was added to a stirred mixture of N-(4-(methoxymethyl) phenyl)nicotinamide (0.50 g, 1.95 mmol) and 1,2,3,5-tetraacetyl-β-D-ribofuranose (1.1 eq) in dry $CH_3CN$ (20 mL). After stirring for 2 h at ambient temperature the solvent was evaporated and residue was taken up in anhydrous MeOH (20 mL), cooled in ice bath and treated with $SOCl_2$ (3.5 eq.) After stirring for 16 h at 5° C., HPLC analysis showed approximately 20% of the mono acetate intermediate still present so additional $SOCl_2$ (1 eq.) was added and stirring was continued for 8 h at 5° C. After workup and purification of the crude product on the ISCO, the product (405 mg, 13%) was isolated as a light yellow solid.

$^1$H NMR ($D_2O$): δ 9.63 (s, 1H), 9.25 (d, 1H), 9.02 (d, 1H), 8.26 (app t, 1H), 7.54 (m, 2H), 7.43 (d, 1H), 7.34 (d, 1H), 6.24 (d, 1H), 4.50 (t, 1H), 4.46 (m, 1H), 4.35 (s, 2H), 3.95 (ab q, 2H). MS(ESI+) m/z=361.1

Example 12: Compound 12

N-(4-(diethylcarbamoyl)phenyl)-1-((2R,3R,4S,5R)-3,4-dihydroxy-5-(hydroxymethyl)tetrahydrofuran-2-yl)-1λ4-pyridine-3-carboxamide

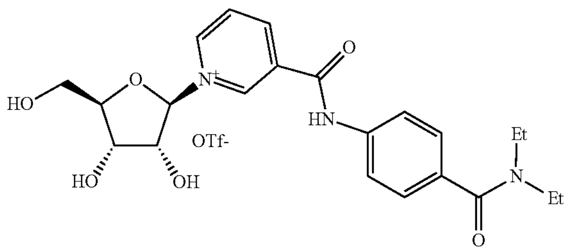 [SMILES: CCN(CC)C(=O)c1ccc(NC(=O)c2ccc[n+]([C@@H]3O[C@H](CO)[C@@H](O)[C@H]3O)c2)cc1]

Following General Procedure B: TMS-triflate (1.2 eq.) was added to a stirred mixture of N-(4-(diethylcarbamoyl)phenyl)nicotinamide (1.4 g, 4.7 mmol) and 1,2,3,5-tetraacetyl-β-D-ribofuranose (1.15 eq.) in DCM (50 mL) followed by 3 h of stirring. Subsequent treatment with $SOCl_2$ (3 eq.) in MeOH and stirring at 5° C. for 16 h gave after workup as previously described, the crude product as a semi-solid mass. The residue was taken up in a minimum of 15% MeOH in DCM and loaded onto a 40 g ISCO column eluting with a gradient of 10% MeOH in DCM to 40% MeOH in DCM to afford the product (1.15 g, 57%) as an off-white solid.

$^1$H NMR ($D_2O$): δ 9.67 (s, 1H), 9.27 (d, 1H), 9.05 (d, 1H), 8.29 (t, 1H), 7.67 (d, 2H), 7.46 (d, 2H), 6.24 (d, 1H), 4.53 (app t, 1H), 4.46 (m, 1H), 4.36 (t, 1H), 3.95 (ab q, 2H), 3.53 (q, 2H), 3.29 (q, 2H), 1.23 (t, 3H), 1.09 (t, 3H). MS(ESI+) m/z=430.2

Example 13: Compound 13

N-(4-cyanophenyl)-1-((2R,3R,4S,5R)-3,4-dihydroxy-5-(hydroxymethyl)tetrahydrofuran-2-yl)-1λ4-pyridine-3-carboxamide

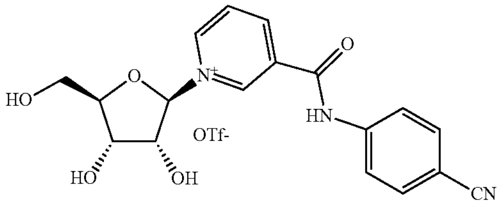 [SMILES: N#Cc1ccc(NC(=O)c2ccc[n+]([C@@H]3O[C@H](CO)[C@@H](O)[C@H]3O)c2)cc1]

Following General Procedure B: TMS-triflate (1.2 eq.) was added to a stirred mixture of N-(4-cyanophenyl)nicotinamide (1.5 g, 5.63 mmol) and 1,2,3,5-tetraacetyl-β-D-ribofuranose (1.1 eq.) in DCM (40 mL) followed by 3 h of stirring at ambient temperature. Evaporation of the solvent followed by treatment with $SOCl_2$ (3 eq.) in MeOH and stirring at 5° C. for 16 h gave after workup as previously described, the crude product as a semi-solid mass. The residue was taken up in a minimum of 20% MeOH in DCM and loaded onto a 40 g ISCO column eluting with a gradient of 10% MeOH in DCM to 40% MeOH in DCM to afford 1.15 g (57%) of the pure product as an off-white solid.

$^1$H NMR ($D_2O$): δ 9.66 (s, 1H), 9.27 (d, 1H), 9.04 (d, 1H), 8.28 (t, 1H), 7.75 (m, 4H), 6.25 (d, 1H), 4.52 (t, 1H), 4.46 (m, 1H), 4.34 (app t, 1H), 4.03 (dd, 1H), 3.95 (ab q, 2H). MS(ESI+) m/z=356.1

Example 14: Compound 14

1-((2R,3R,4S,5R)-3,4-dihydroxy-5-(hydroxymethyl)tetrahydrofuran-2-yl)-N-(4-(trifluoromethyl)phenyl)-1λ4-pyridine-3-carboxamide

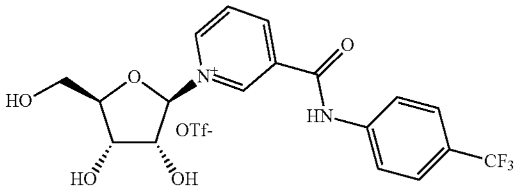 [SMILES: O=C(Nc1ccc(C(F)(F)F)cc1)c1ccc[n+]([C@@H]2O[C@H](CO)[C@@H](O)[C@H]2O)c1]

Following General Procedure B: TMS-triflate (1.5 mL, 8.04 mmol, 1.2 eq.) was added to a stirred mixture of N-(4-(trifluoromethyl)phenyl)nicotinamide (1.5 g, 6.7 mmol) and 1,2,3,5-tetraacetyl-β-D-ribofuranose (2.4 g, 7.4 mmol, 1.1 eq.) in DCM (40 mL). Subsequent treatment with $SOCl_2$ (3 eq.) in MeOH and stirring at 5° C. for 16 h followed by workup as previously described, gave the crude product as an off-white solid. One half of this material was chromatographed on the ISCO (40 g cartridge, elution with a gradient of DCM to 30% MeOH in DCM) to give the product (300 mg) as a white solid.

$^1$H NMR ($D_2O$): δ 9.66 (s, 1H), 9.27 (d, 1H), 9.04 (d, 1H), 8.28 (t, 1H), 7.75 (m, 4H), 6.25 (d, 1H), 4.52 (t, 1H), 4.46 (m, 1H), 4.34 (app t, 1H), 4.03 (dd, 1H), 3.95 (ab q, 2H). MS(ESI+) m/z=399.1

Example 15: Compound 15

4-(1-((2R,3R,4S,5R)-3,4-dihydroxy-5-(hydroxymethyl)tetrahydrofuran-2-yl)-1λ4-pyridine-3-carboxamido)benzoic acid

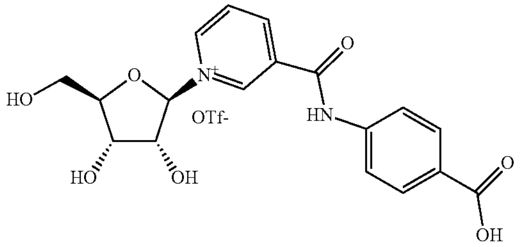 [SMILES: O=C(O)c1ccc(NC(=O)c2ccc[n+]([C@@H]3O[C@H](CO)[C@@H](O)[C@H]3O)c2)cc1]

To a mixture of 4-(nicotinamido)benzoic acid (3.76 g, 9.59 mmol) and 1,2,3,5-tetraacetyl-β-D-ribofuranose (3.20 g, 10.07 mmol) in dry dioxane (40 mL) was added triethylamine (4.02 mL, 28.8 mmol, 3 eq.) and the mixture was stirred for 15 minutes at room temperature. TMS-triflate (6.94 mL, 38.4 mmol, 3 eq.) was added over 5 minutes and the reaction was allowed to stir for 20 min, whereupon HPLC analysis showed the reaction to be complete. The mixture was diluted with 40 mL of MTBE and the solution was poured into 300 mL of MTBE and the resultant oil was allowed to settle. After decanting the solvent, the oil was triturated twice with 80 mL portions of MTBE. The residue was dissolved in EtOAc (50 mL) and washed with 2×30 mL portions of water and dried over anhydrous $Na_2SO_4$. Filtration and evaporation of the solvent yielded 5.5 g of the crude triacetate intermediate. 2.23 g of this material was chromatographed on 600 g of silica gel eluting with a gradient of 5% MeOH in DCM to 30% MeOH in DCM to provide the purified triacetate (1.3 g) as a white solid.

Triacetate: $^1H$ NMR ($CD_3CN$): δ 9.68 (br s, 1H), 9.48 (d, 1H), 9.14 (d, 1H), 9.09 (dd, 1H), 8.33 (dd, 1H), 8.10 (d, 2H), 7.92 (d, 2H), 6.45 (m, 1H), 5.53 (d, 1H), 5.43 (t, 1H), 4.81 (q, 1H), 4.53 (dd, 1H), 4.50 (dd, 1H), 2.19 (s, 3H), 2.14 (s, 3H), 2.11 (s, 3H).

The triacetate (1.3 g, 2.0 mmol) was dissolved in 4 mL of dry MeOH and was added to a well-stirred ice-cold solution of 1N NaOMe in MeOH (6 mL, 6.0 mmol, 3 eq.) under Ar. The mixture was stirred for 20 min. then a cold solution 1N HCl in MeOH (6 mL, 6.0 mmol, 3 eq.) was added all at once. The color of the solution changed from dark orange to yellow and a solid precipitated from solution (the pH of the solution was 2). The product was filtered and washed generously with MTBE then dried under high vacuum to provide the product (369 mg, 49%) as a light pink solid.

$^1H$ NMR ($D_2O$): δ 9.65 (s, 1H), 9.27 (d, 1H), 9.03 (d, 1H), 8.28 (t, 1H), 8.01 (q, 2H), 7.71 (br d, 2H), 6.25 (d, 1H), 4.52 (t, 1H), 4.47 (q, 1H), 4.35 (t, 1H), 4.03 (dd, 1H), 3.88 (dd, 1H). MS(ESI+) m/z=375.1

Example 16: Compound 16

Methyl 2-chloro-4-(1-((2R,3R,4S,5R)-3,4-dihydroxy-5-(hydroxymethyl)tetrahydrofuran-2-yl)-1λ$^4$-pyridine-3-carboxamido)benzoate

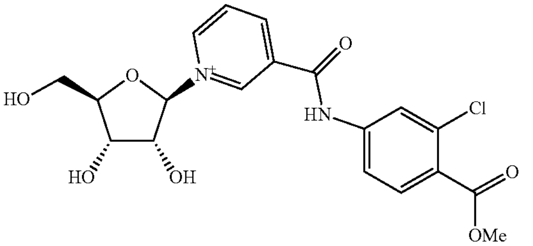 [SMILES: COC(=O)c1ccc(NC(=O)c2ccc[n+]([C@@H]3O[C@H](CO)[C@@H](O)[C@H]3O)c2)cc1Cl]

Following General Procedure B: TMS-triflate (1.2 eq.) was added to a stirred mixture of methyl 2-chloro-4-(nicotinamido)benzoate (610 mg, 2.31 mmol) and 1,2,3,5-tetraacetyl-β-D-ribofuranose (1.1 eq.) in DCM (40 mL). After stirring for 2 h, 20 mL of dry $CH_3CN$ was added to give a clear solution and the reaction mixture was stirred an additional hour at ambient temperature. The solvent was removed under reduced pressure and the residue was dissolved in MeOH, cooled and treated with $SOCl_2$ (3 eq.) in MeOH. The mixture was stirred for 16 h and workup as described previously furnished the crude product which was purified on the ISCO to afford a white solid (600 mg, 26%).

$^1H$ NMR ($D_2O$): δ 9.64 (s, 1H), 9.28 (d, 1H), 9.03 (d, 1H), 8.29 (app t, 1H), 7.87 (d, 1H), 7.82 (d, 1H), 7.57 (dd, 1H), 6.24 (d, 1H), 4.52 (app t, 1H), 4.46 (m, 1H), 4.34 (app t, 1H), 4.03 (app dd, 1H), 3.95 (ab q, 2H). MS(ESI+) m/z=423.1

Example 17: Compound 17

1-((2R,3R,4S,5R)-3,4-dihydroxy-5-(hydroxymethyl)tetrahydrofuran-2-yl)-N-(4-(oxazol-2-yl)phenyl)-1λ$^4$-pyridine-3-carboxamide

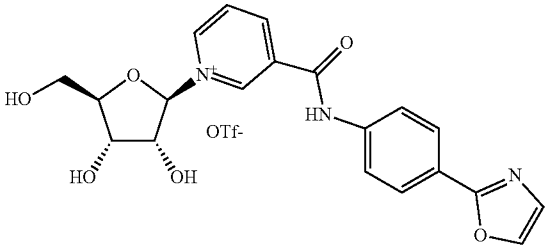 [SMILES: O=C(Nc1ccc(-c2ncco2)cc1)c1ccc[n+]([C@@H]2O[C@H](CO)[C@@H](O)[C@H]2O)c1]

Following General Procedure B: TMS-triflate (1.2 eq.) was added to a stirred mixture of N-(4-(oxazol-2-yl)phenyl)nicotinamide (900 mg, 3.4 mmol) and 1,2,3,5-tetraacetyl-β-D-ribofuranose (1.2 g, 3.73 mmol, 1.1 eq.) in dry acetonitrile (40 mL) for 2 h. After removal of the solvent under reduced pressure the residue was dissolved in MeOH and treated with 3 eq. of $SOCl_2$ and stirred at 5° C. for 16 h. Subsequent workup as previously described, gave the crude product as a tan solid. Purification on the ISCO (40 g cartridge, gradient elution with DCM to 30% MeOH in DCM) afforded the product as a white solid (650 mg, 48%).

$^1H$ NMR ($D_2O$): δ 11.74 (br s, 1H), 9.81 (br s, 1H), 9.46 (d, 1H), 9.26 (d, 1H), 8.40 (t, 1H), 8.23 (d, 1H), 8.03-8.12 (m, 5H), 7.37 (br s, 1H), 6.25 (d, 1H), 4.43 (t, 1H), 4.28 (m, 1H), 4.20 (t, 1H), 3.79 (ab q, 2H). MS(ESI+) m/z=398.1

Example 18: Compound 18

1-((2R,3R,4S,5R)-3,4-dihydroxy-5-(hydroxymethyl)tetrahydrofuran-2-yl)-N-(2-methyl-1,3-dioxoisoindolin-5-yl)-1λ$^4$-pyridine-3-carboxamide

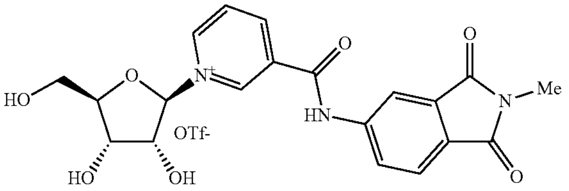 [SMILES: CN1C(=O)c2ccc(NC(=O)c3ccc[n+]([C@@H]4O[C@H](CO)[C@@H](O)[C@H]4O)c3)cc2C1=O]

Following General Procedure B: TMS-triflate (1.91 mL, 10.34 mmol, 1.2 eq.) was added to a stirred mixture of N-(2-methyl-1,3-dioxoisoindolin-5-yl)nicotinamide (2.46 g, 8.75 mmol) and 1,2,3,5-tetraacetyl-β-D-ribofuranose (3.04 g, 9.56 mmol, 1.1 eq.) in $CH_3CN$ (80 mL). After stirring for 3 h at ambient temperature followed by removal of the solvent and treatment with $SOCl_2$ (3 eq.) in MeOH and stirring for 16 h, the crude product was obtained as a tan solid after trituration with MTBE. Purification was accomplished on the ISCO (40 g cartridge, elution with a gradient of DCM to 30% MeOH in DCM). After combining the pure fractions and evaporation of the solvents under reduced pressure, the product (1.05 g, 29%) was obtained as an off-white solid.

$^1H$ NMR ($D_2O$): δ 9.69 (s, 1H), 9.31 (d, 1H), 9.07 (d, 1H), 8.34 (t, 1H), 8.08 (s, 1H), 7.83 (dd, 2H), 6.26 (d, 1H), 4.53 (t, 1H), 4.46 (m, 1H), 4.36 (t, 1H), 3.95 (ab q, 2H), 3.07 (s, 3H). MS(ESI+) m/z=414.1

Example 19: Compound 19

1-((2R,3R,4S,5R)-3,4-dihydroxy-5-(hydroxymethyl)tetrahydrofuran-2-yl)-N-(2-methyl-3-oxoisoindolin-5-yl)-1λ$^4$-pyridine-3-carboxamide

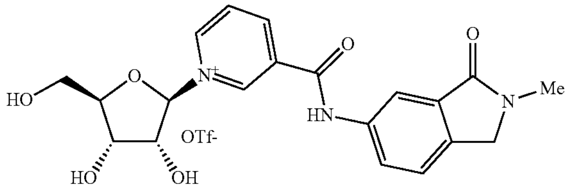 [SMILES: CN1Cc2ccc(NC(=O)c3ccc[n+]([C@@H]4O[C@H](CO)[C@@H](O)[C@H]4O)c3)cc2C1=O]

Following General Procedure B: TMS-triflate (1.2 eq.) was added to a stirred mixture of N-(2-methyl-3-oxoisoindolin-5-yl) nicotinamide (1.25 g, 4.7 mmol) and 1,2,3,5-tetraacetyl-β-D-ribofuranose (1.1 eq.) in dry $CH_3CN$ (50 mL). After stirring for 3 h at ambient temperature followed by evaporation of the solvent and treatment with $SOCl_2$ (3 eq.) in MeOH for 24 h at 5° C., the crude product was obtained as an off-white solid after trituration. Purification on the ISCO (40 g cartridge, elution with a gradient of DCM to 40% MeOH in DCM) afforded the pure product (650 mg, 35%) as a white solid.

$^1H$ NMR ($D_2O$): δ 9.65 (s, 1H), 9.28 (d, 1H), 9.04 (d, 1H), 8.30 (t, 1H), 7.83 (s, 1H), 7.83 (s, 1H), 7.66 (d, 1H), 7.57 (d, 1H), 6.26 (d, 1H), 5.42 (s, 1H), 4.53 (t, 1H), 4.46 (m, 1H), 3.95 (ab q, 2H), 3.10 (s, 1H). MS(ESI+) m/z=400.2

Example 20: Compound 20

N-(3-carbamoylphenyl)-1-((2R,3R,4S,5R)-3,4-dihydroxy-5-(hydroxymethyl)tetrahydrofuran-2-yl)-1λ$^4$-pyridine-3-carboxamide

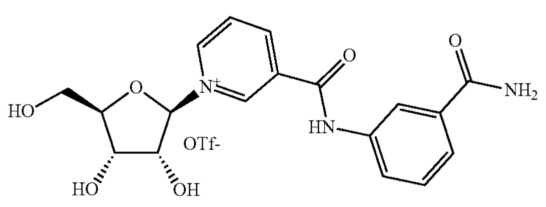 [SMILES: NC(=O)c1cccc(NC(=O)c2ccc[n+]([C@@H]3O[C@H](CO)[C@@H](O)[C@H]3O)c2)c1]

TMS-triflate (1.3 mL, 7.1 mmol, 1.2 eq.) was added to a stirred mixture of N-(3-carbamoylphenyl)nicotinamide (1.42 g, 6.75 mmol) and 1,2,3,5-tetraacetyl-β-D-ribofuranose (2.2 g, 6.8 mmol, 1.1 eq.) in $CH_3CN$ (60 mL) at room temperature. After stirring for 2 h, the solvent was removed and the residue was taken up in ethyl acetate. The solution was transferred to a separatory funnel and washed sequentially with an aqueous solution of 5% $NaHCO_3$, water and brine then dried over anhydrous $Na_2SO_4$. The solution was filtered and concentrated and the residue was purified on the ISCO (40 g cartridge) eluting with DCM to 20% MeOH in DCM. The fractions containing the product were pooled and concentrated to give the triacetate intermediate (405 mg) as a foam. This material was dissolved in dry MeOH (20 mL), cooled in an ice bath and treated with 3 equiv. of $SOCl_2$. The solution was stirred at 5° C. for 24 h. The solution was triturated with MTBE to precipitate the product as a white solid which was collected by filtration. The product was washed on the vacuum funnel with several portions of MTBE then placed under high vacuum to remove traces of HCl. The product (140 mg, 6%) was obtained as a white solid.

$^1H$ NMR ($D_2O$): δ 9.68 (s, 1H), 9.28 (d, 1H), 9.05 (d, 1H), 8.29 (t, 1H), 7.97 (s, 1H), 7.76 (d, 1H), 7.68 (d, 1H), 7.56 (t, 1H), 6.25 (d, 1H), 4.51 (app t, 1H), 4.47 (m, 1H), 4.36 (t, 1H), 3.95 (ab q, 2H). MS(ESI+) m/z=374.1

Example 21: Compound 21

1-((2R,3R,4S,5R)-3,4-dihydroxy-5-(hydroxymethyl)tetrahydrofuran-2-yl)-N-(3-oxo-1,3-dihydroisobenzofuran-5-yl)-1λ$^4$-pyridine-3-carboxamide

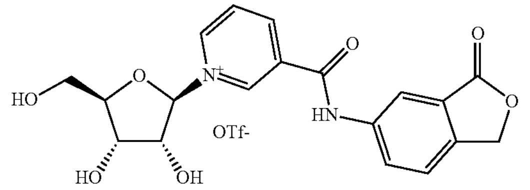 [SMILES: O=C(Nc1ccc2c(c1)C(=O)OC2)c1ccc[n+]([C@@H]2O[C@H](CO)[C@@H](O)[C@H]2O)c1]

Following General Procedure B: TMS-triflate (0.75 mL, 4.1 mmol, 1.2 eq) was added to a stirred mixture of N-(3-oxo-1,3-dihydroisobenzofuran-5-yl) nicotinamide (0.85 g, 3.4 mmol) and 1,2,3,5-tetraacetyl-β-D-ribofuranose (1.2 g, 3.7 mmol, 1.1 eq.) in $CH_3CN$ (25 mL). After stirring for 1.5 h at ambient temperature followed by removal of the solvent and treatment with $SOCl_2$ (3.5 eq.) in MeOH, the solution was stirred for 24 h at 5° C. MTBE was added slowly to the solution to precipitate the crude product which was triturated with MTBE and the residue co-stripped with DCM followed by $CH_3CN$ to remove traces of HCl. The residue was dissolved in a minimum of 20% MeOH in DCM and loaded onto a 24 g ISCO cartridge. Elution with 5% to 30% MeOH in DCM followed by evaporation of the pure fractions gave the pure product (505 mg, 38%).

$^1H$ NMR ($D_2O$): δ 9.68 (s, 1H), 9.28 (d, 1H), 9.06 (d, 1H), 8.32 (t, 1H), 8.12 (s, 1H), 7.89 (d, 1H), 7.66 (d, 1H), 6.26 (d, 1H), 5.43 (s, 2H), 4.54 (t, 1H), 4.46 (m, 1H), 4.36 (t, 1H). MS(ESI+) m/z=387.1

Example 22: Compound 22

Methyl 1-(1-((2R,3R,4S,5R)-3,4-dihydroxy-5-(hydroxymethyl)tetrahydrofuran-2-yl)-1λ$^4$-pyridine-3-carbonyl)indoline-5-carboxylate

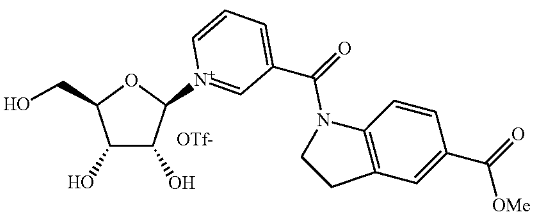 [SMILES: COC(=O)c1ccc2c(c1)CCN2C(=O)c1ccc[n+]([C@@H]2O[C@H](CO)[C@@H](O)[C@H]2O)c1]

Following General Procedure B: TMS-triflate (1.2 eq.) was added to a stirred mixture of methyl 1-nicotinoylindoline-5-carboxylate (0.5 g, 1.78 mmol) and 1,2,3,5-tetraacetyl-β-D-ribofuranose (1.1 eq.) in $CH_3CN$ (16 mL). After stirring for 2 h at ambient temperature the solvent was removed and the residue was dissolved in MeOH, cooled and treated with $SOCl_2$ (3 eq.). After stirring for 16 h at 5° C. the crude product was obtained after trituration with MTBE as an off-white solid. Purification was accomplished in the normal fashion on the ISCO (40 g cartridge, elution with a gradient of 10% MeOH in DCM to 30% MeOH in DCM) to furnish the product (330 mg, 45%) as an off-white solid.

$^1H$ NMR ($D_2O$): δ 9.45 (br s, 1H), 9.25 (d, 1H), 8.85 (d, 1H), 8.3 (t, 1H), 7.70-8.10 (m, 3H), 6.23 (br s, 1H), 4.47 (m, 2H), 4.35 (m, 1H), 3.92-4.20 (m, 3H), 3.85 (s, 3H), 3.16 (m, 2H). MS(ESI+) m/z=415.2

Example 23: Compound 23

Methyl (4-(1-((2R,3R,4S,5R)-3,4-dihydroxy-5-(hydroxymethyl)tetrahydrofuran-2-yl)-1λ$^4$-pyridine-carboxamido benzoyl)glycinate

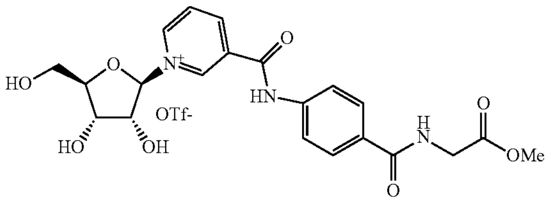 [SMILES: COC(=O)CNC(=O)c1ccc(NC(=O)c2ccc[n+]([C@@H]3O[C@H](CO)[C@@H](O)[C@H]3O)c2)cc1]

Following General Procedure B: TMS-triflate (1.2 eq.) was added to a stirred mixture of methyl (4-(nicotinamido) benzoyl)glycinate (0.5 g, 1.6 mmol) and 1,2,3,5-tetraacetyl-β-D-ribofuranose (1.1 eq.) in $CH_3CN$ (15 mL). After stirring for 2 h at ambient temperature, removal of the solvent and treatment with $SOCl_2$ (3.5 eq.) in MeOH, the solution was stirred for 16 h at 5° C. HPLC at that time showed 10% of the mono-acetate remaining so additional $SOCl_2$ (0.1 mL) was added and stirring was continued for 6 h. The crude product was obtained after trituration with MTBE as an off-white solid. Purification on the ISCO (12 g cartridge, elution with a gradient of 5% MeOH in DCM to 30% MeOH in DCM) furnished the product (155 mg, 22%) as an off-white solid.

$^1H$ NMR ($D_2O$): δ 9.65 (br s, 1H), 9.26 (d, 1H), 9.03 (m, 1H), 8.27 (t, 1H), 7.65-7.88 (m, 4H), 6.24 (d, 1H), 4.50 (t, 1H), 4.45 (t, 1H), 4.35 (m, 1H), 4.15 (br s, 1H), 3.95 (ab q), 3.75 (s, 3H). MS(ESI+) m/z=446.2

Example 24: Compound 24

Ethyl 4-(1-((2R,3R,4S,5R)-3,4-dihydroxy-5-(hydroxymethyl)tetrahydrofuran-2-yl)-1λ$^4$-pyridine-3-carboxamido)benzoate

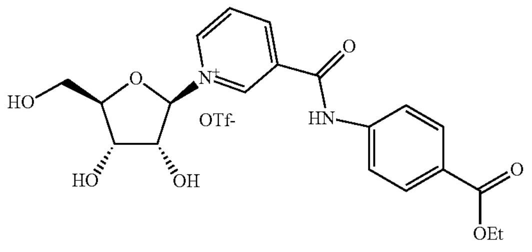 [SMILES: CCOC(=O)c1ccc(NC(=O)c2ccc[n+]([C@@H]3O[C@H](CO)[C@@H](O)[C@H]3O)c2)cc1]

Following General Procedure B: TMS-triflate (1.2 eq.) was added to a stirred mixture of ethyl 4-(nicotinamido) benzoate (0.5 g, 1.85 mmol) and 1,2,3,5-tetraacetyl-β-D-ribofuranose (1.1 eq.) in $CH_3CN$ (20 mL). After stirring for 3 h at ambient temperature the solvent was evaporated and residue was taken up in anhydrous absolute EtOH (20 mL) and cooled in an ice bath. $SOCl_2$ (3.5 eq.) was added dropwise and the solution was allowed to stand at 5° C. for 72 h. Workup as previously described gave the crude product as a semi-solid mass. The crude product was purified on the ISCO (24 g cartridge, loading with 10% MeOH in DCM) eluting with a gradient of 5-30% MeOH in DCM over 15 min. The pure fractions were pooled, stripped and traces of solvent were removed under high vacuum. The product (145 mg, 19%) was obtained as an off-white solid.

$^1H$ NMR (DMSO$d_6$): δ 11.75 (s, 1H), 9.79 (s, 1H), 9.46 (d, 1H), 8.38 (t, 1H), 8.04 (m, 4H), 6.24 (d, 1H), 4.42 (t, 1H), 4.22-4.35 (m, 3H), 4.18 (t, 1H), 3.80 (ab q, 2H), 1.33 (t, 3H). MS(ESI+) m/z=403.2

Example 25: Compound 25

Methyl 51-((2R,3R,4S,5R)-3,4-dihydroxy-5-(hydroxymethyl)tetrahydrofuran-2-yl)-1?$^4$-pyridine-3-carboxamido)picolinate

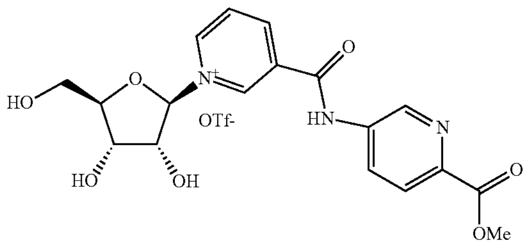

Following General Procedure B: TMS-triflate (1.2 eq.) was added to a stirred mixture of methyl 5-(nicotinamido) picolinate (1.21 g, 4.8 mmol) and 1,2,3,5-tetraacetyl-β-D-ribofuranose (1.1 eq) in $CH_3CN$ (50 mL). After stirring for 3 h at ambient temperature, the solvent was evaporated and residue was taken up in anhydrous MeOH (40 mL), cooled in an ice bath and treated with $SOCl_2$ (3.5 eq.) After stirring at 5° C. for 24 h, the solution was concentrated to 10 mL and the product was precipitated with MTBE. The product was filtered through a sintered glass funnel and washed sequentially with 2×5 mL portions of ice-cold MeOH then an excess of MTBE. After removing traces of solvent under high vacuum, the product (650 mg, 35%) was isolated as a white solid.

$^1H$ NMR ($D_2O$): δ 9.63 (s, 1H), 9.26 (d, 1H), 9.03 (d, 1H), 8.26 (app t, 1H), 7.84 (br s, 1H), 7.70 (m, 1H), 7.59 (m, 1H), 6.23 (d, 1H), 4.47 (t, 1H), 4.42 (s, 3H), 4.33 (app t, 1H), 3.94 (ab q, 2H). MS(ESI+) m/z=390.1

Example 26: Compound 26

1-((2R,3R,4S,5R)-3,4-dihydroxy-5-(hydroxymethyl)tetrahydrofuran-2-yl)-N-(1-oxoisoindolin-5-yl)-1λ$^4$-pyridine-3-carboxamide

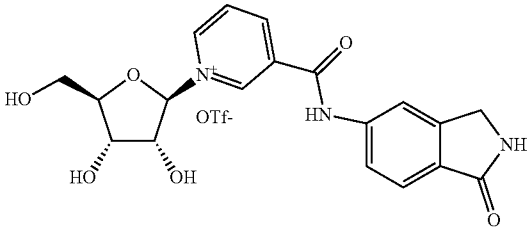 [SMILES: O=C(Nc1ccc2c(c1)CNC2=O)c1ccc[n+]([C@@H]2O[C@H](CO)[C@@H](O)[C@H]2O)c1]

Following General Procedure A: TMS-triflate (1.2 eq.) was added to a stirred mixture of N-(1-oxoisoindolin-5-yl)nicotinamide (0.56 g, 2.2 mmol) and 1,2,3,5-tetraacetyl-β-D-ribofuranose (1.1 eq) in $CH_3CN$ (20 mL). After stirring for 1.5 h at ambient temperature, the solvent was evaporated and residue was taken up in anhydrous MeOH (20 mL) and cooled in an ice bath. $SOCl_2$ (3.5 eq.) was added dropwise and the solution was stirred at 5° C. for 18 h. The product was precipitated with MTBE, the solvents were decanted and the solids were re-dissolved in MeOH and precipitated with MTBE. After trituration with MTBE, the solids (hygroscopic) were co-evaporated with $CH_3CN$ to remove traces of water and HCl. The pure product (600 mg, 71%) was obtained as an off-white solid.

$^1$H NMR (DMSO-$d_6$): δ 11.9 (br s, 1H), 9.81 (d, 1H), 9.27 (app d, 1H), 9.16 (app d, 1H), 8.48 (m, 1H), 8.43 (app t, 1H), 8.18 (d, 1H), 6.24 (d, 1H), 4.40 (app t, 1H), 4.29 (m, 1H), 4.19 (app t, 1H), 3.87 (s, 2H), 3.81 (ab q, 2H). MS(ESI+) m/z=386.1

Example 27: Compound 27

2-(dimethylamino)ethyl 4-(1-((2R,3R,4S,5R)-3,4-dihydroxy-5-(hydroxymethyl)tetra hydrofuran-2-yl)-1λ$^4$-pyridine-3-carboxamido)benzoate

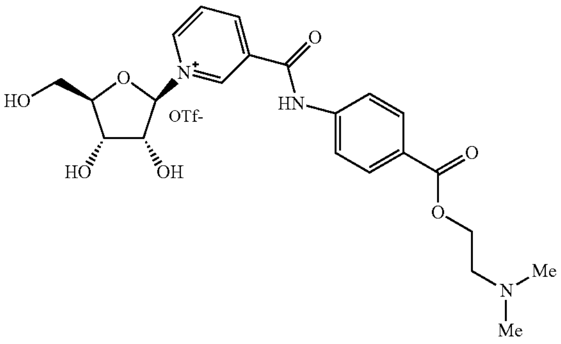 [SMILES: CN(C)CCOC(=O)c1ccc(NC(=O)c2ccc[n+]([C@@H]3O[C@H](CO)[C@@H](O)[C@H]3O)c2)cc1]

TMS-triflate (3.0 g, 13.7 mmol) was added over 5 min. to a stirred solution of 2-(dimethylamino)ethyl 4-(nicotinamido)benzoate (1.8 g, 5.7 mmol) and 1,2,3,5-tetraacetyl-β-D-ribofuranose (1.8 g, 5.7 mmol) in 40 mL of DCM in an ice bath. The reaction mixture was allowed to warm to ambient temperature and stirred overnight. The solvent was stripped and the residue was dissolved in EtOAc. This was washed with water, saturated $NaHCO_3$ and brine, then dried over $Na_2SO_4$ and evaporated to dryness under vacuum to give 2.5 g of the triacetate as a solid. This compound was dissolved in 25 mL of dry MeOH and after cooling in an ice bath was treated with 1.63 g (20.8 mmol, 3.65 eq.) of acetyl chloride dropwise. The mixture was placed under argon and allowed to stand at 10° C. overnight then was allowed to warm to ambient temperature and stirred for 3 h. The solvent was stripped to near dryness and the residue was triturated with hexanes (2×150 mL) followed by MTBE (3×100 mL). The residue was taken up in MeOH (10 mL) and evaporated under high vacuum to give 2.1 g of a solid. The solid was suspended in 250 mL of acetone and treated with aqueous 5% $NaHCO_3$ to neutrality. After standing in the freezer for several hours, the mixture was filtered, the filtrate was evaporated to an oil, frozen and lyophilized to give the product (650 mg, 43%) as a brown solid.

$^1$H NMR ($D_2O/CD_3CN$): δ 10.0 (s, 1H), 9.6 (s, 1H), 9.4 (dd, 1H), 8.7 (s, 1H), 8.5 (d, 2H), 8.2 (d, 2H), 6.5 (d, 1H), 4.75 (m, 4H), 4.3 (m, 1H), 4.2 (m, 1H), 3.4 (m, 2H), 2.9 (s, 6H). MS(ESI+) m/z=446.2

Example 28: Compound 28

1-((2R,3R,4S,5R)-3,4-dihydroxy-5-(hydroxymethyl)tetrahydrofuran-2-yl)-N-(4-(N,N-dimethylsulfamoyl)phenyl)-1λ$^4$-pyridine-3-carboxamide

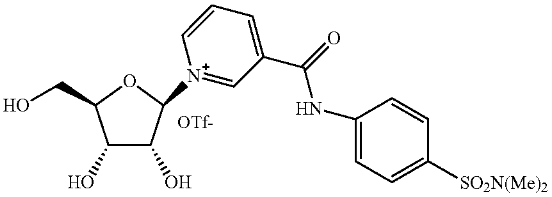

Following General Procedure A: TMS-triflate (1.2 eq.) was added to a stirred mixture of N-(4-(N,N-dimethylsulfamoyl)phenyl)nicotinamide (0.55 g, 1.8 mmol) and 1,2,3,5-tetraacetyl-β-D-ribofuranose (1.1 eq) in $CH_3CN$ (20 mL). After stirring for 2 h at ambient temperature the solvent was evaporated and residue was taken up in anhydrous MeOH (20 mL) and cooled in an ice bath. $SOCl_2$ (3.5 eq.) was added dropwise and the solution was allowed to stand in the freezer at −5° C. for 72 h. The solution was brought to room temperature and the product was precipitated with MTBE. The solvents were decanted from the product and the solids were dissolved in 5 mL of MeOH and allowed to stir at ambient temperature for 1 h. A fine white precipitate formed which was filtered in a sintered glass funnel and washed with ice-cold MeOH (5 mL) followed by MTBE. The pure product (220 mg, 28%) was obtained as an off-white solid.

$^1$H NMR ($D_2O$): δ 9.68 (br s, 1H), 9.28 (d, 1H), 9.05 (d, 1H), 8.29 (t, 1H), 7.83 (m, 4H), 6.25, (d, 1H), 4.43-4.57 (m, 2H), 4.36 (t, 1H), 3.95 (ab q, 2H), 2.65 (s, 6H). MS(ESI+) m/z=438.1

Example 29: Compound 29

Methyl 2-(4-(1-((2R,3R,4S,5R)-3,4-dihydroxy-(hydroxymethyl)tetrahydrofuran-2-yl)-1λ[4]-pyridine-3-carboxamido)phenyl)acetate

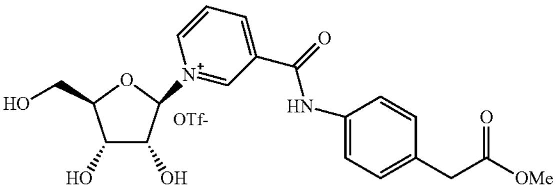 [SMILES: COC(=O)Cc1ccc(NC(=O)c2ccc[n+]([C@@H]3O[C@H](CO)[C@@H](O)[C@H]3O)c2)cc1]

Following General Procedure B: TMS-triflate (1.2 eq.) was added to a stirred mixture of methyl 2-(4-(nicotinamido)phenyl)acetate (0.50 g, 1.85 mmol) and 1,2,3,5-tetraacetyl-β-D-ribofuranose (1.1 eq.) in DCM (20 mL). After stirring for 30 min HPLC analysis of an aliquot showed only about 20% conversion, so additional TMS-triflate (1.2 eq.) was added. The reaction mixture was stirred at ambient temperature for 1.5 h and the solvent was evaporated and the residue was taken up in anhydrous MeOH (20 mL). $SOCl_2$ (3.5 eq.) was added dropwise to the solution at 0° C. and the reaction mixture was allowed to stir at 5° C. for 16 h. HPLC analysis at that time showed about 25% of the mono and diacetate intermediates present so additional $SOCl_2$ (1 eq.) was added and stirring was continued for an additional 5 h. Workup as described previously and purification on the ISCO in the usual fashion gave the product (340 mg, 46%).

$^1$H NMR ($D_2O$): δ 9.65 (s, 1H), 9.26 (d, 1H), 9.04 (d, 1H), 8.27 (t, 1H), 7.45 (d, 2H), 7.35 (d, 2H), 6.24 (d, 1H), 4.52 (app t, 1H), 4.46 (m, 1H), 4.35 (t, 1H), 3.94 (ab q, 2H), 3.74 (s, 2H), 3.68 (s, 3H). MS(ESI+) m/z=403.2

Example 30: Compound 30

1-((2R,3R,4S,5R)-3,4-dihydroxy-5-(hydroxymethyl)tetrahydrofuran-2-yl)-N-(4-(oxazol-5-yl)phenyl)-1λ[4]-pyridine-3-carboxamide

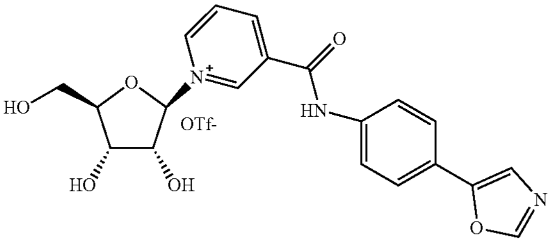 [SMILES: O=C(Nc1ccc(-c2cnco2)cc1)c1ccc[n+]([C@@H]2O[C@H](CO)[C@@H](O)[C@H]2O)c1]

Following General Procedure A: TMS-triflate (1.2 eq.) was added to a stirred mixture of N-(4-(oxazol-5-yl)phenyl)nicotinamide (1.1 g, 4.2 mmol) and 1,2,3,5-tetraacetyl-β-D-ribofuranose (1.1 eq) in $CH_3CN$ (40 mL). After stirring for 2 h at ambient temperature the solvent was evaporated and residue was taken up in anhydrous MeOH (20 mL) and cooled in an ice bath. After treatment with thionyl chloride (3.5 eq.) followed by stirring at 5° C. overnight, the product precipitated from solution. The solids were collected by filtration and washed 2×5 mL portions of ice-cold MeOH followed by a large volume of MTBE. The solids were dried under high vacuum for several hours to afford 0.54 g (32%) of product as a light yellow solid.

$^1$H NMR (DMSO-$d_6$): δ 9.56 (s, 1H), 9.23 (d, 1H), 8.94 (d, 1H), 8.22 (m, 2H), 7.62 (q, 4H), 7.39 (s, 1H), 6.19 (d, 1H), 4.46 (m, 2H), 4.34 (t, 1H), 3.94 (ab q, 2H). MS(ESI+) m/z=398.1

Example 31: Compound 31

Methyl 6-(1-((2R,3R,4S,5R)-3,4-dihydroxy-5-(hydroxymethyl)tetrahydrofuran-2-yl)-1λ[4]-pyridine-3-carboxamido)nicotinate

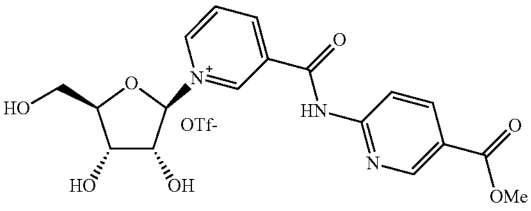 [SMILES: COC(=O)c1ccc(NC(=O)c2ccc[n+]([C@@H]3O[C@H](CO)[C@@H](O)[C@H]3O)c2)nc1]

Following General Procedure A: TMS-triflate (1.2 eq.) was added to a stirred mixture of methyl 6-(nicotinamido)nicotinate (0.50 g, 1.95 mmol) and 1,2,3,5-tetraacetyl-β-D-ribofuranose (1.1 eq) in dry $CH_3CN$ (20 mL). After stirring for 2 h at ambient temperature the solvent was evaporated and residue was taken up in anhydrous MeOH (20 mL) and cooled in an ice bath. The mixture was treated with $SOCl_2$ (3.5 eq.) and stirred at 5° C. for 16 h. HPLC at time still showed about 10% of a mixture of the mono and di-acetate intermediates so additional $SOCl_2$ (1 eq.) was added and stirring was continued for 5 h. The product was precipitated by the addition of MTBE giving a white solid which was triturated with MTBE several times. The crude product was re-dissolved in 10 mL of dry MeOH and precipitated with MTBE as before. The product was filtered and washed with 2×5 mL portions of ice-cold MeOH followed by a large volume of MTBE. After drying under high vacuum for several hours, the product was obtained as a white solid (100 mg, 13%).

$^1$H NMR ($D_2O$): δ 9.72 (s, 1H), 9.28 (d, 1H), 9.08 (d, 1H), 8.93 (app d, 1H), 8.44 (dd, 1H), 8.32 (t, 1H), 8.10 (app d, 4H), 6.25 (d, 1H), 4.53 (t, 1H), 4.46 (m, 1H), 4.34 (t, 1H), 3.95 (ab q, 2H), 3.92 (s, 3H). MS(ESI+) m/z=390.1

Example 32: Compound 32

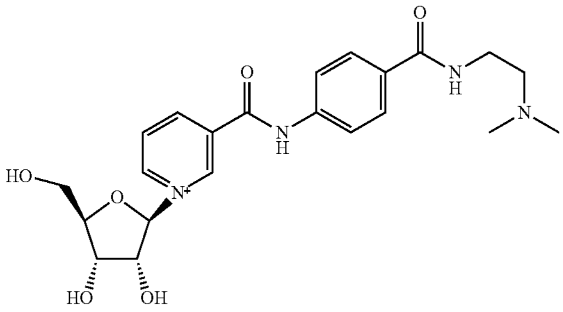 [SMILES: CN(C)CCNC(=O)c1ccc(NC(=O)c2ccc[n+]([C@@H]3O[C@H](CO)[C@@H](O)[C@H]3O)c2)cc1]

Following General Procedure B: TMS-triflate (1.2 eq.) is added to a stirred mixture of the corresponding nicotinamido compound (1.6 mmol) and 1,2,3,5-tetraacetyl-β-D-ribofuranose (1.1 eq.) in $CH_3CN$ (15 mL). After stirring for 2 h at ambient temperature, removal of the solvent and treatment with $SOCl_2$ (3.5 eq.) in MeOH, the solution is stirred for 16 h at 5° C. If HPLC shows 10% of the mono-acetate remaining, additional $SOCl_2$ (0.1 mL) is added and stirring is continued for 6 h. The crude product is obtained after trituration with MTBE as a solid. Purification on the ISCO (12 g cartridge, elution with a gradient of 5% MeOH in DCM to 30% MeOH in DCM) furnishes the product as a solid.

Example 33: Compound 33

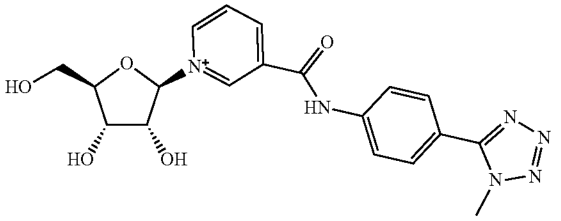 [SMILES: Cn1nnnc1-c1ccc(NC(=O)c2ccc[n+]([C@@H]3O[C@H](CO)[C@@H](O)[C@H]3O)c2)cc1]

Following General Procedure B: TMS-triflate (1.2 eq.) is added to a stirred mixture of the corresponding nicotinamido compound (1.6 mmol) and 1,2,3,5-tetraacetyl-β-D-ribofuranose (1.1 eq.) in $CH_3CN$ (15 mL). After stirring for 2 h at ambient temperature, removal of the solvent and treatment with $SOCl_2$ (3.5 eq.) in MeOH, the solution is stirred for 16 h at 5° C. If HPLC shows 10% of the mono-acetate remaining, additional $SOCl_2$ (0.1 mL) is added and stirring is continued for 6 h. The crude product is obtained after trituration with MTBE as a solid. Purification on the ISCO (12 g cartridge, elution with a gradient of 5% MeOH in DCM to 30% MeOH in DCM) furnishes the product as a solid.

Example 34: Compound 34

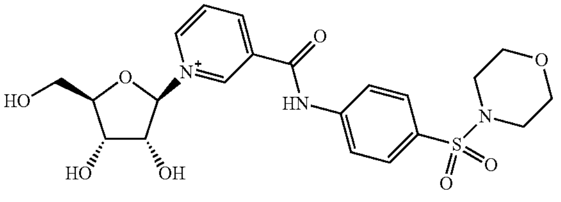 [SMILES: O=C(Nc1ccc(S(=O)(=O)N2CCOCC2)cc1)c1ccc[n+]([C@@H]2O[C@H](CO)[C@@H](O)[C@H]2O)c1]

Following General Procedure B: TMS-triflate (1.2 eq.) is added to a stirred mixture of the corresponding nicotinamido compound (1.6 mmol) and 1,2,3,5-tetraacetyl-β-D-ribofuranose (1.1 eq.) in $CH_3CN$ (15 mL). After stirring for 2 h at ambient temperature, removal of the solvent and treatment with $SOCl_2$ (3.5 eq.) in MeOH, the solution is stirred for 16 h at 5° C. If HPLC shows 10% of the mono-acetate remaining, additional $SOCl_2$ (0.1 mL) is added and stirring is continued for 6 h. The crude product is obtained after trituration with MTBE as a solid. Purification on the ISCO (12 g cartridge, elution with a gradient of 5% MeOH in DCM to 30% MeOH in DCM) furnishes the product as a solid.

Example 35: Compound 35

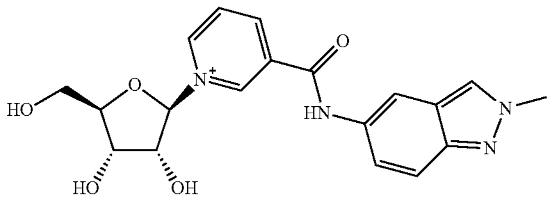 [SMILES: Cn1cc2cc(NC(=O)c3ccc[n+]([C@@H]4O[C@H](CO)[C@@H](O)[C@H]4O)c3)ccc2n1]

Following General Procedure B: TMS-triflate (1.2 eq.) is added to a stirred mixture of the corresponding nicotinamido compound (1.6 mmol) and 1,2,3,5-tetraacetyl-β-D-ribofuranose (1.1 eq.) in $CH_3CN$ (15 mL). After stirring for 2 h at ambient temperature, removal of the solvent and treatment with $SOCl_2$ (3.5 eq.) in MeOH, the solution is stirred for 16 h at 5° C. If HPLC shows 10% of the mono-acetate remaining, additional $SOCl_2$ (0.1 mL) is added and stirring is continued for 6 h. The crude product is obtained after trituration with MTBE as a solid. Purification on the ISCO (12 g cartridge, elution with a gradient of 5% MeOH in DCM to 30% MeOH in DCM) furnishes the product as a solid.

Example 36: Compound 36

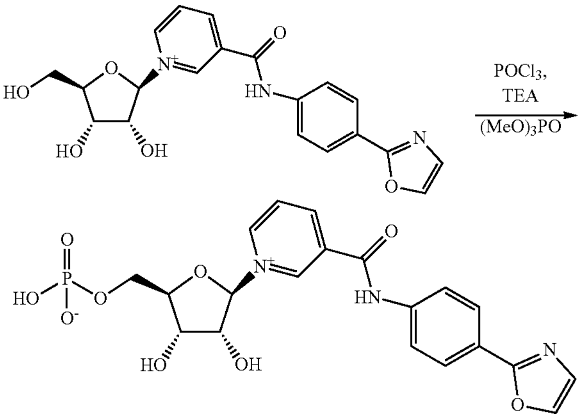

A dry 100 mL flask is charged with 4.1 mmol of Compound 17. The flask is flushed with argon and 10 mL of trimethylphosphate is added. The resulting solution is cooled to 0° C. and treated with $POCl_3$ (8.2 mmol, 2 eq.). The flask is sealed and allowed to stand in the freezer at −10° C. After 2.5 h the homogeneous solution is treated with triethylamine (2.0 mmol) over several minutes and allowed to stand in the freezer overnight. The reaction mixture is cooled in an ice bath and the well-stirred suspension is treated with water (82 mmol) over several minutes followed by solid $NaHCO_3$ (28.7 mmol) and stirring is continued for 90 min. at 0° C. The reaction mixture is treated with 100 mL of $CH_3CN$ containing 33 mmol of 90% formic acid to produce a solid. The solid is recovered by filtration, washed with $CH_3CN$ and placed under high vacuum to give a crude product. This material is purified by medium pressure chromatography on a column containing 50 g of aminopropyl functionalized silica. The product is dissolved in 25 mL of 60%/40% MeOH—$CH_3CN$ containing 100 mM formic acid and the column is equilibrated with the same solvent mixture. The product-containing fractions are combined and concentrated; co-evaporated from water (3×25 mL), frozen and lyophilized to give the product.

Example 37: Compound 37

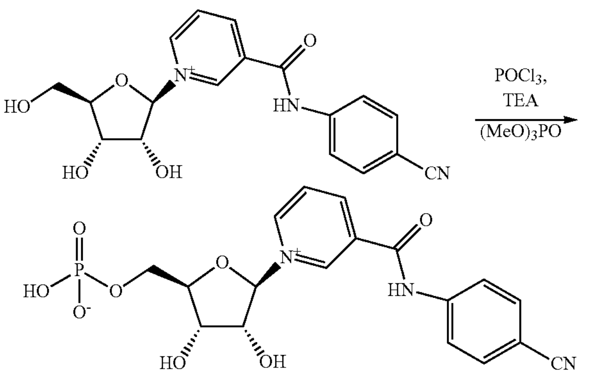

A dry 100 mL flask is charged with 4.1 mmol of Compound 13. The flask is flushed with argon and 10 mL of trimethylphosphate is added. The resulting solution is cooled to 0° C. and treated with $POCl_3$ (8.2 mmol, 2 eq.). The flask is sealed and allowed to stand in the freezer at −10° C. After 2.5 h the homogeneous solution is treated with triethylamine (2.0 mmol) over several minutes and allowed to stand in the freezer overnight. The reaction mixture is cooled in an ice bath and the well-stirred suspension is treated with water (82 mmol) over several minutes followed by solid $NaHCO_3$ (28.7 mmol) and stirring is continued for 90 min. at 0° C. The reaction mixture is treated with 100 mL of $CH_3CN$ containing 33 mmol of 90% formic acid to produce a solid. The solid is recovered by filtration, washed with $CH_3CN$ and placed under high vacuum to give a crude product. This material is purified by medium pressure chromatography on a column containing 50 g of aminopropyl functionalized silica. The product is dissolved in 25 mL of 60%/40% MeOH—$CH_3CN$ containing 100 mM formic acid and the column is equilibrated with the same solvent mixture. The product-containing fractions are combined and concentrated; co-evaporated from water (3×25 mL), frozen and lyophilized to give the product.

Biological Assays

Example B1: General Assay $2\times10^3$ Hek293 (human embryonic kidney) and HepG2 (human hepatocellular carcinoma) cells plated per well in 96 well clear bottom black plate adhere O/N. The following day cells were treated with 2 mM NMN or 500 μM other compounds, and after 24 hours of treatment, cells were analyzed with CellTiter-Fluor and NAD assay.

Figure 1B:
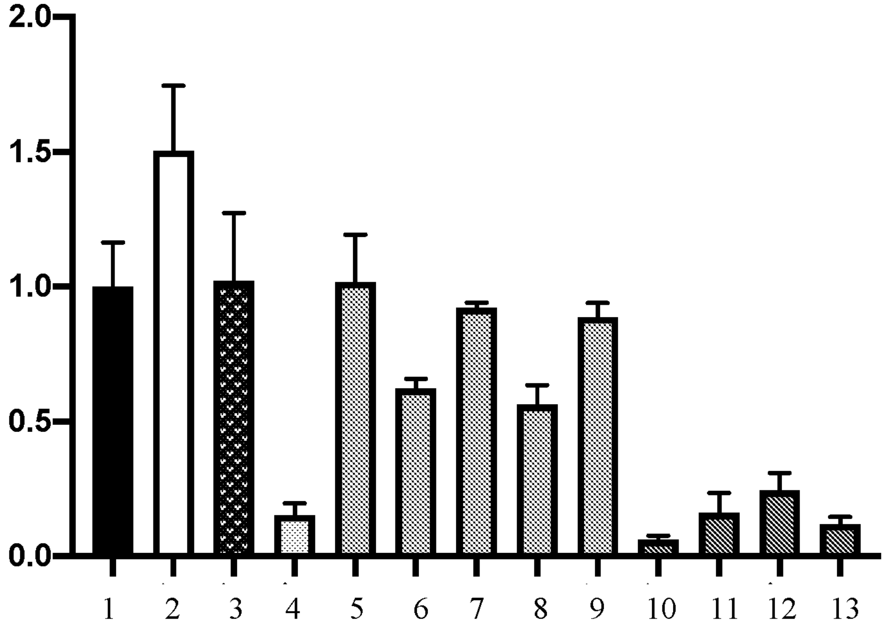

FIG. 1A and FIG. 1B depict NAD(H) in cells upon treatment with control or compounds according to Formula 1. FIG. 1A is from Hek293 cells (human embryonic kidney cells), while FIG. 1B is from HepG2 cells (human hepatocellular carcinoma cells).

For both FIG. 1A and FIG. 1B, the Y-axis is the amount of NAD(H)/number of viable cells, normalized to 1.0 for no treatment; and the X-axis is as follows:

1: (control)—no treatment
2: (control)—treatment with nicotinamide mononucleotide (NMN)
3: (control)—treatment with PABA-methyl
4: Treatment with Compound 1
5: (control)—treatment with Compound A
6: Treatment with Compound 9
7: Treatment with Compound 7
8: Treatment with Compound 8
9: Treatment with Compound 6
10: Treatment with Compound 2
11: Treatment with Compound 4
12: Treatment with Compound 3
13: Treatment with Compound 5

Figure 2A:
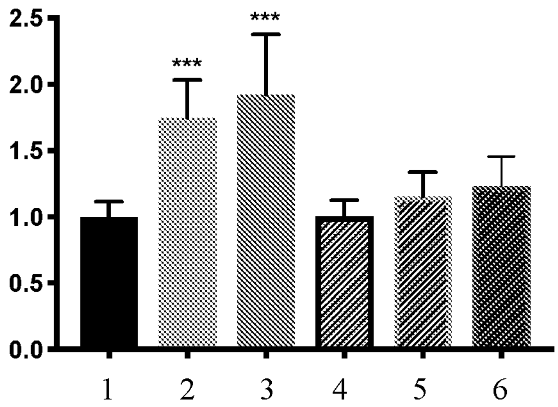
FIG. 2A, FIG. 2B, and FIG. 2C depict NAD(H) in normal cells upon treatment with control or a compound according to Formula 1.
Figure 2B:
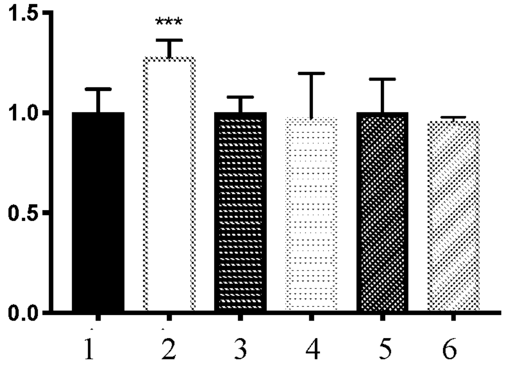
Figure 2C:
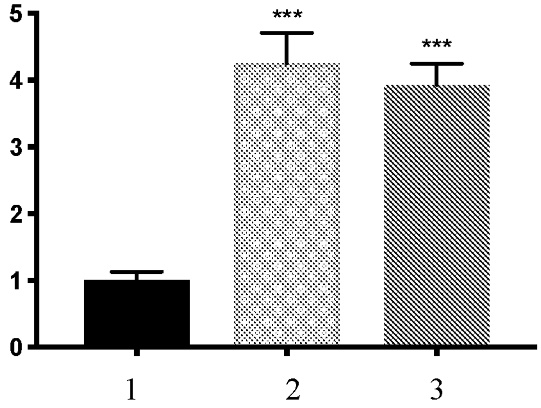

Example B2: FIG. 2A, FIG. 2B, and FIG. 2C depict NAD(H) in normal cells upon treatment with control or Compound 1, according to Formula 2a. FIG. 2A is from AML12 (2K/well) cells (murine normal hepatocytes), while FIG. 2B is from Hek293 cells (human embryonic kidney cells), and FIG. 2C is from primary hPBMC cells (human peripheral blood mononuclear cells). For FIG. 2A and FIG. 2B, the Y-axis is the amount of NAD(H)/number of viable cells, normalized to 1.0 for no treatment. For FIG. 2C, the Y-axis shows pg NAD(H)/micrograms total protein, normalized to 1.0 for no treatment.

In FIG. 2A, the X-axis is as follows:

1: (control)—no treatment
2: (control)—treatment with nicotinamide mononucleotide (NMN), 2 mM
3: (control)—treatment with nicotinamide mononucleotide (NMN), 0.5 mM
4: (control)—treatment with ethanol
5: Treatment with Compound 1, 0.5 mM
6: Treatment with Compound 1, 0.25 mM In FIG. 2B, the X-axis is as follows:

1: (control)—no treatment
2: (control)—treatment with nicotinamide mononucleotide (NMN), 800 μM
3: (control)—no treatment (Prep 1)
4: Treatment with Compound 1, 800 μM (Prep 1)
5: (control)—no treatment (Prep 2)
6: Treatment with Compound 1, 800 μM (Prep 2)

Figure 3A:
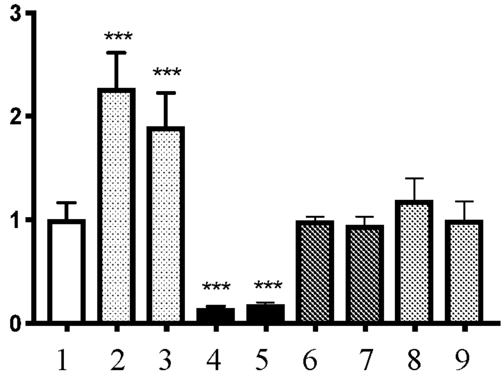
FIG. 3A, FIG. 3B, FIG. 3C, and FIG. 3D depict NAD(H) in cancer cells upon treatment with control or a compound according to Formula 1.
Figure 3C:
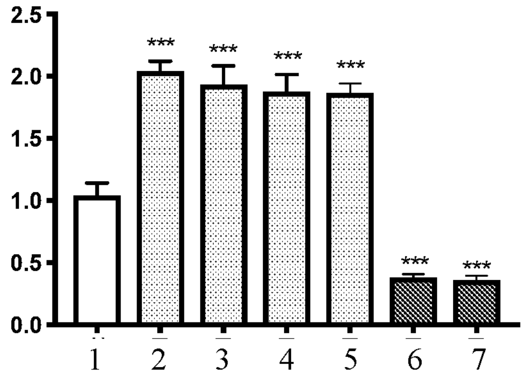
Figure 3B:
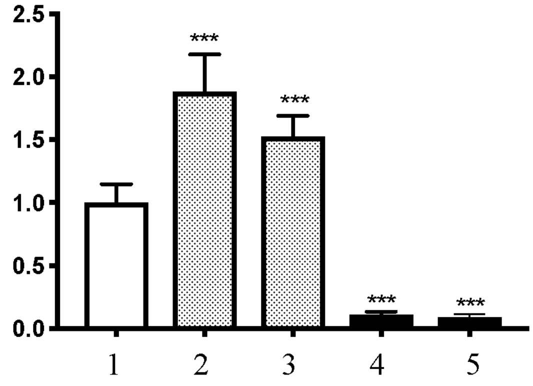
Figure 3D:
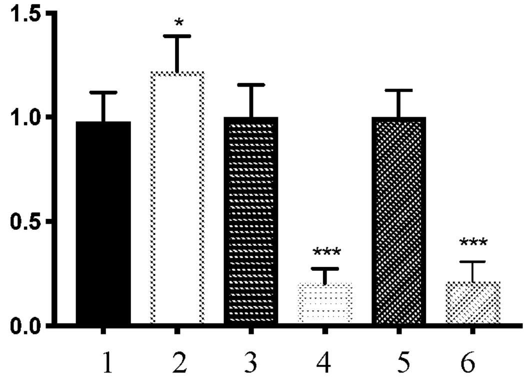

In FIG. 2C, the X-axis is as follows:

1: (control)—no treatment
2: (control)—treatment with nicotinamide mononucleotide (NMN), 1 mM
3: Treatment with Compound 1, 1 mM Example B3: FIG. 3A, FIG. 3B, FIG. 3C, and FIG. 3D depict NAD(H) in cancer cells upon treatment with control or Compound 1, according to Formula 1. FIG. 3A is from B16-F10 cells (murine melanoma), while FIG. 3B is from RAW264.7 cells (murine tumor-derived macrophages), FIG. 3C is from Jurkat cells (human acute T cell leukemia), and FIG. 3D is from HepG2 cells (human hepatocellular carcinoma). For FIG. 3B and FIG. 3D, the Y-axis is the amount of NAD(H)/number of viable cells, normalized to 1.0 for no treatment. For FIG. 3A and FIG. 3C, the Y-axis is pg NAD(H)/μg total protein, normalized to 1.0 for no treatment.

In FIG. 3A, the X-axis is as follows:

1: (control) no treatment
2: (control) NMN 1 mM
3: (control) NMN 250 μM
4: Compound 1, 250 μM
5: Compound 1, 500 μM
6: (control) PABA, 250 μM
7: (control) PABA, 500 μM
8: (control) PABA Methyl Ester, 250 μM
9: (control) PABA Methyl Ester, 500 μM In FIG. 3B, the X-axis is as follows:

1: (control) no treatment

2: (control) NMN, 2 mM

3: (control) NMN, 500 μM

4: Compound 1, 500 μM

5: Compound 1, 250 μM

In FIG. 3C, the X-axis is as follows:

1: (control) no treatment

2: (control) NMN, 2 mM

3: (control) NMN, 1 mM

4: (control) NMN, 500 μM

5: (control) NMN, 250 μM

6: Compound 1, 500 μM

7: Compound 1, 250 μM

In FIG. 3D, the X-axis is as follows:

1: (control) no treatment

2: (control) NMN 800 μM

3: (control) no treatment (Prep 1)

4: Compound 1, 800 μM (Prep 1)

5: (control) no treatment (Prep 2)

6: Compound 1, 800 μM (Prep 2)

Figure 4A:
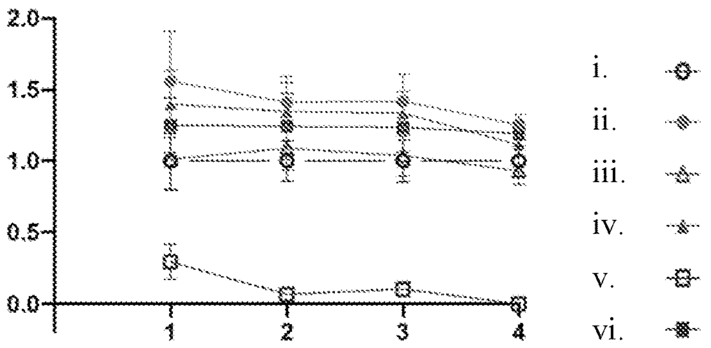
FIG. 4A and FIG. 4B depict NAD(H) level and viability in normal cells (Hek293 cells/human embryonic kidney cells) upon treatment with control or a compound according to Formula 1, as a measure of cytotoxicity/cytostasis.
Figure 4B:
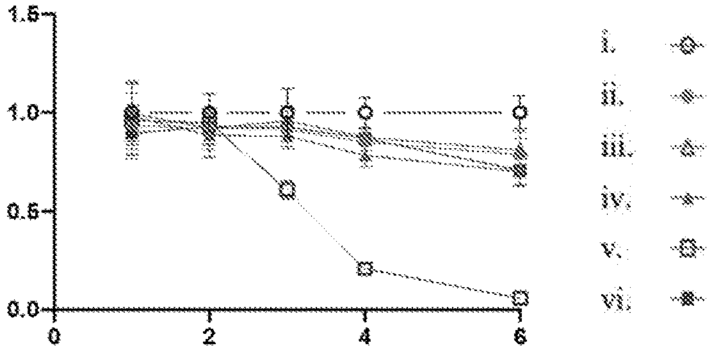

Example B4: FIG. 4A and FIG. 4B depict NAD(H) level and viability in normal cells (Hek293 cells/human embryonic kidney cells) upon treatment with control or Compound 1, according to Formula 1, as a measure of cytotoxicity/cytostasis. In FIG. 4A, the Y-axis shows the amount of NAD(H)/number of viable cells, normalized to 1.0 for no treatment, and the X-axis reflects the number of days of treatment. In FIG. 4B, the Y-axis shows the cell number as a measure of viability normalized to 1.0 for no treatment, and the X-axis reflects the number of days.

Figure 5A:
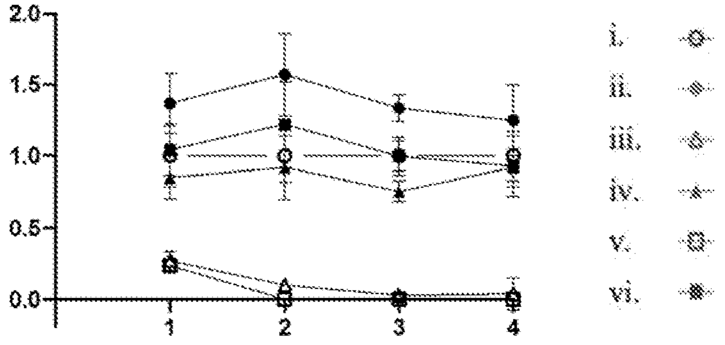
FIG. 5A and FIG. 5B depict NAD(H) level and viability in cancer cells (HepG2 cells/human hepatocellular carcinoma) upon treatment with control or a compound according to Formula 1, as a measure of cytotoxicity/cytostasis.
Figure 5B:
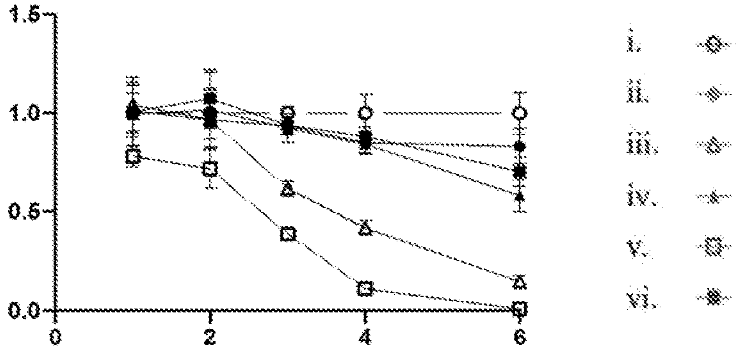

Example B5: FIG. 5A and FIG. 5B depict NAD(H) level and viability in cancer cells (HepG2 cells/human hepatocellular carcinoma) upon treatment with control or Compound 1, according to Formula 1, as a measure of cytotoxicity/cytostasis. In FIG. 5A, the Y-axis shows the amount of NAD(H)/number of viable cells, normalized to 1.0 for no treatment, and the X-axis reflects the number of days of treatment. In FIG. 5B, the Y-axis shows the cell number as a measure of viability normalized to 1.0 for no treatment, and the X-axis reflects the number of days.

For FIG. 4A, FIG. 4B, FIG. 5A, and FIG. 5B, the following legend applies:

i. (Control) Untreated ii. (Control) Nicotinamide mononucleotide (NMN)

iii. Compound 1 iv. Compound 1+NMN v. (Control) FK866 vi. (Control) FK866+NMN

Example B6: General Assay for FIG. 6A and FIG. 6B: 2×103 Hek293 (human embryonic kidney) and HepG2 (human hepatocellular carcinoma) cells plated per well in 96 well clear bottom black plate adhere O/N. The following day, cells were treated with 2 mM NMN or 250 μM other compounds, after 24 hour of treatment cells analyzed with CellTiter-Fluor and NAD assay.

Figure 6A:
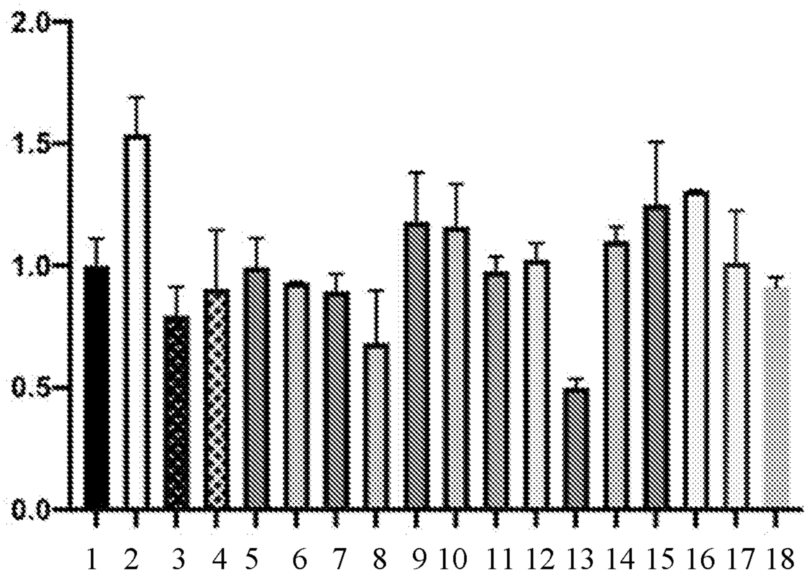
FIG. 6A and FIG. 6B depict NAD(H) in cells upon treatment with control or compounds according to Formula 1.

FIG. 6A depicts NAD(H) level in normal cells (Hek293 cells/human embryonic kidney cells) upon treatment with control or various compounds. In FIG. 6A, the Y-axis shows the amount of NAD(H)/number of viable cells, normalized to 1.0 for no treatment.

Figure 6B:
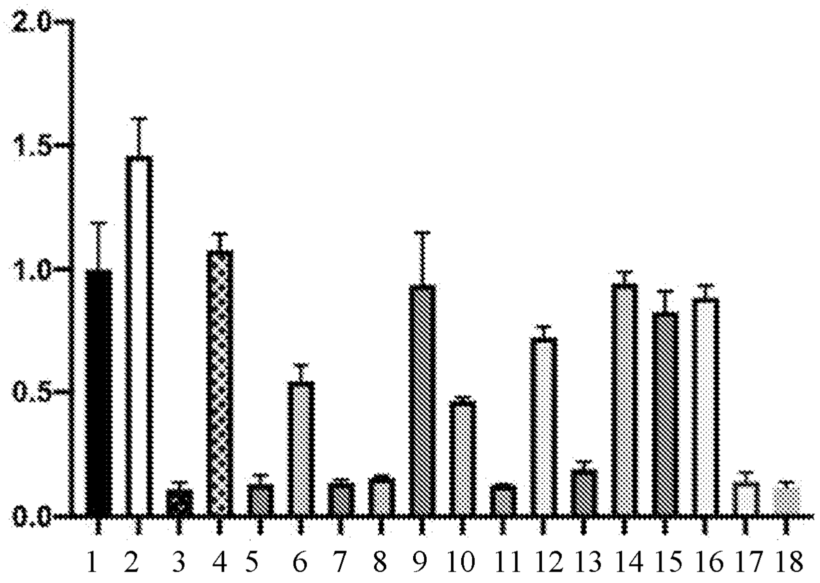

FIG. 6B depicts NAD(H) level in cancer cells (HepG2 cells/human hepatocellular carcinoma) upon treatment with control or various compounds. In FIG. 6B, the Y-axis shows the amount of NAD(H)/number of viable cells, normalized to 1.0 for no treatment.

In both FIG. 6A and FIG. 6B, the X-axis is as follows:

1: (control)—no treatment

2: (control)—treatment with nicotinamide mononucleotide (NMN)

3: (control)—treatment with PABA-nicotinamide (PABA nicotinate methyl ester)

4: (control)—treatment with DMSO vehicle

5: Treatment with Compound 1

6: Treatment with Compound 12

7: Treatment with Compound 13

8: Treatment with Compound 14

9: Treatment with Compound 15

10: Treatment with Compound 16

11: Treatment with Compound 17

12: Treatment with Compound 18

13: Treatment with Compound 19

14: Treatment with Compound 20

15: Treatment with Compound 21

16: Treatment with Compound 22

17: Treatment with Compound 23

18: Treatment with Compound 24

The invention claimed is:

1. A compound having the structure of Formula 2c:

2c

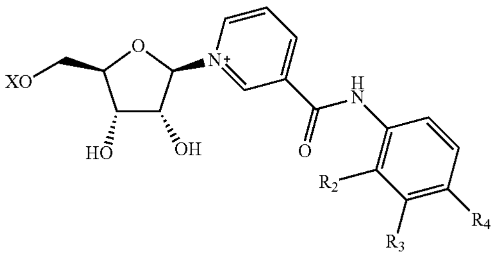

or a salt thereof, wherein

X is H or a phosphate group;

$R_2$ is selected from H, a halogen, a carboxylic acid, a substituted or unsubstituted $C_1$-$C_6$ carboxy ester, a substituted or unsubstituted $C_1$-$C_6$ alkyl group, a substituted or unsubstituted $C_1$-$C_6$ alkoxy group, a substituted or unsubstituted $C_1$-$C_6$ alkenyl group, and a substituted or unsubstituted $C_1$-$C_6$ alkynyl group;

$R_3$ is selected from H, a halogen, a substituted or unsubstituted $C_1$-$C_6$ alkyl group, a substituted or unsubstituted $C_1$-$C_6$ alkenyl group, a substituted or unsubstituted $C_1$-$C_6$ alkynyl group, a substituted or unsubstituted $C_1$-$C_6$ alkoxy group, a carboxylic acid, a substituted or unsubstituted $C_1$-$C_6$ carboxy ester, and a substituted or unsubstituted carboxamide; and $R_4$ is selected from H, a substituted or unsubstituted $C_1$-$C_6$ alkyl group, a substituted or unsubstituted $C_1$-$C_6$ alkenyl group, a substituted or unsubstituted $C_1$-$C_6$ alkynyl group, a substituted or unsubstituted $C_1$-$C_6$ alkoxy group, a carboxylic acid, a substituted or unsubstituted $C_1$-$C_6$ carboxy ester, and a substituted or unsubstituted carboxamide;

and further wherein at least one of $R_2$ and $R_3$ is not H.

2. The compound of claim 1, selected from:

7

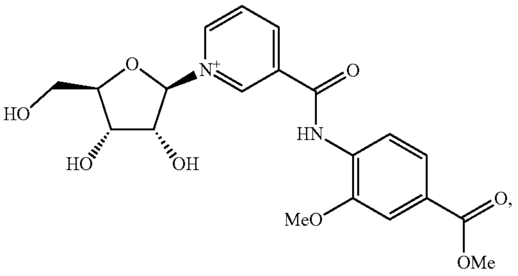

8

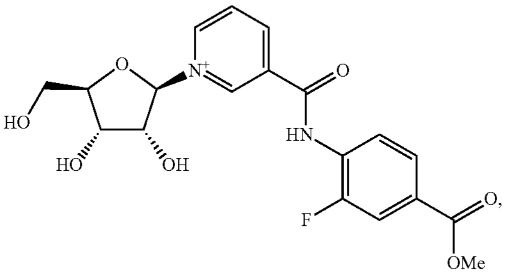

9

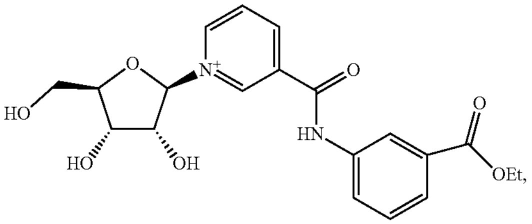

10

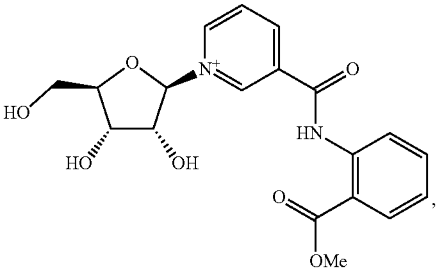

16

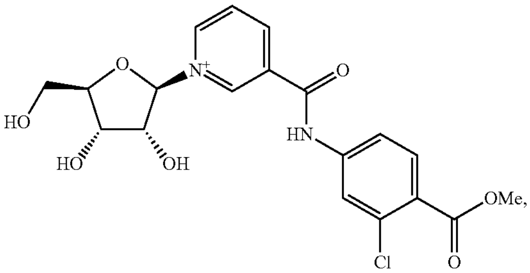

and

-continued

20

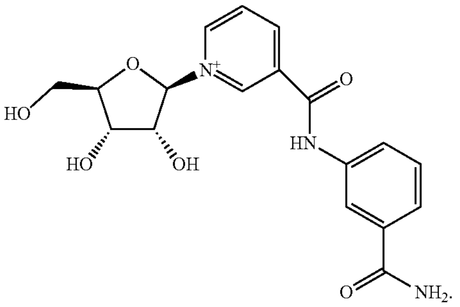

3. The compound according to claim 1, wherein said salt is formed with a cation selected from $H^+$, $Li^+$, $Na^+$, $K^+$, $Mg^{2+}$, and $Ca^{2+}$ and/or said salt is formed with an anion selected from acetate, trifluoromethansulfonate (triflate), halide, trifluoroacetate, formate, $H_2PO_4^-$, $HPO_4^{2-}$, $OH^-$, $HSO_4^-$, $SO_4^{2-}$, $NO_3^-$, $HCO_3^-$, and $CO_3^{2-}$ or said salt is a zwitterion.

4. A composition comprising the compound according to claim 1, and a pharmaceutically acceptable excipient or carrier.

5. A method of differentially modulating nicotinamide adenine dinucleotide (NAD) levels in two or more tissues or cell types, said method comprising administering a compound according to claim 1 or a composition comprising said compound, wherein said administering induces a differential response in NAD levels in a first tissue or cell type and a second tissue or cell type.

6. The method of claim 5, wherein said differential response in NAD levels is selected from at least a 10% difference in NAD levels, at least a 20% difference in NAD levels, at least a 30% difference in NAD levels, at least a 40% difference in NAD levels, and at least a 50% difference in NAD levels.

7. The method of claim 5, wherein said differential response in NAD levels is an increase in NAD levels of at least 10% in said first tissue or cell type compared to untreated NAD levels, and a simultaneous decrease in NAD levels of at least 10% in said second tissue or cell type compared to untreated NAD levels.

8. The method of claim 5, wherein said differential response in NAD levels is a maintenance in NAD levels within 10% in said first tissue or cell type compared to untreated NAD levels, and a simultaneous decrease in NAD levels of at least 10% in said second tissue or cell type compared to untreated NAD levels.

9. The method of claim 5, wherein said method is a treatment of cancer in an individual in need thereof.

10. A method of treating or suppressing cancer in an individual in need thereof, said method comprising administering a compound according to claim 1 or a composition comprising said compound.

11. A method of increasing or maintaining healthy tissue or cells in an individual in need thereof while suppressing the growth of neoplastic or cancerous tissue or cells, said method comprising administering a compound according to claim 1 or a composition comprising said compound.

12. A method of synthesizing a compound according to claim 1, comprising reacting an amine-containing precursor with a nicotinic riboside precursor under conditions to condense said precursors to yield a compound according to claim 1.

* * * * *